(12) United States Patent
Pukkila-Worley

(10) Patent No.: US 10,729,690 B2
(45) Date of Patent: Aug. 4, 2020

(54) ANTIHELMINTHIC MEDICATIONS FOR PATHOGENIC NEMATODES

(71) Applicant: UNIVERSITY OF MASSACHUSETTS, Boston, MA (US)

(72) Inventor: Read Pukkila-Worley, Cambridge, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/069,399

(22) PCT Filed: Jan. 12, 2017

(86) PCT No.: PCT/US2017/013227
§ 371 (c)(1),
(2) Date: Jul. 11, 2018

(87) PCT Pub. No.: WO2017/123787
PCT Pub. Date: Jul. 20, 2017

(65) Prior Publication Data
US 2019/0091225 A1    Mar. 28, 2019

Related U.S. Application Data

(60) Provisional application No. 62/278,208, filed on Jan. 13, 2016.

(51) Int. Cl.
| | | |
|---|---|---|
| *A61K 31/517* | (2006.01) | |
| *C12N 15/113* | (2010.01) | |
| *A61P 33/10* | (2006.01) | |
| *A01K 67/033* | (2006.01) | |

(52) U.S. Cl.
CPC ............ *A61K 31/517* (2013.01); *A61P 33/10* (2018.01); *C12N 15/1138* (2013.01); *A01K 67/0336* (2013.01); *A01K 2207/05* (2013.01); *A01K 2217/03* (2013.01); *C12N 15/1137* (2013.01); *C12N 2310/14* (2013.01); *C12Y 207/11001* (2013.01)

(58) Field of Classification Search
None
See application file for complete search history.

(56) References Cited

U.S. PATENT DOCUMENTS

| 5,705,188 A | 1/1998 | Junichi et al. ................ 424/450 |
|---|---|---|
| 2008/0194503 A1 | 8/2008 | Monia et al. .................... 514/44 |
| 2010/0068172 A1 | 3/2010 | De Craen ...................... 800/285 |
| 2012/0232110 A1 | 9/2012 | Moy et al. ............... 514/252.01 |

FOREIGN PATENT DOCUMENTS

| WO | WO/1997/030731 | 8/1997 |
|---|---|---|
| WO | WO/2012/078949 | 6/2012 |

OTHER PUBLICATIONS

Ayres, J. S. et al. (2008) "A Signaling Protease Required for Melanization in *Drosophila* Affects Resistance and Tolerance of Infections," *PLoS Biology* 6(12), e305.
Ayres, J. S. et al. (2009) "The Role of Anorexia in Resistance and Tolerance to Infections in *Drosophila,*" *PLoS Biology* 7(7), e1000150.
Ayres, J. S. et al. (2012) "Tolerance of Infections," *Annual Review of Immunology* 30(1), 271-294.
Berg, T. (2003) "Modulation of Protein—Protein Interactions with Small Organic Molecules," *Angewandte Chemie International Edition* 42(22), 2462-2481.
Bolz, D. D. et al. (2010) "A Conserved PMK-1/p38 MAPK Is Required in Caenorhabditis elegans Tissue-specific Immune Response to Yersinia pestis Infection," *Journal of Biological Chemistry* 285(14), 10832-10840.
Calfon, M. et al. (2002) "IRE1 couples endoplasmic reticulum load to secretory capacity by processing the XBP-1 mRNA," *Nature* 415, 92.
Cappello, M. et al. (2006) "A purified *Bacillus thuringiensis* crystal protein with therapeutic activity against the hookworm parasite *Ancylostoma ceylanicum,*" *Proceedings of the National Academy of Sciences* 103(41), 15154.
Cheesman, H. K. et al. (2016) "Aberrant Activation of p38 MAP Kinase-Dependent Innate Immune Responses is Toxic to *Caenorhabditis elegans,*" *G3: Genes |Genomes|Genetics* 6(3), 541-549.
Cohen, L. B. et al. (2015) "Microbial pathogenesis and host defense in the nematode C. elegans," *Current Opinion in Microbiology* 23, 94-101.
Ding, W. et al. (2015) "s-Adenosylmethionine Levels Govern Innate Immunity through Distinct Methylation-Dependent Pathways," *Cell Metabolism* 22(4), 633-645.
Hu, Y. et al. (2010) "Bacillus thuringiensis Cry5B Protein Is Highly Efficacious as a Single-Dose Therapy against an Intestinal Roundworm Infection in Mice," *PLoS Neglected Tropical Diseases* 4(3), e614.
Hu, Y. et al. (2010) "Discovery of a highly synergistic anthelmintic combination that shows mutual hypersusceptibility," *Proceedings of the National Academy of Sciences* 107(13), 5955.

(Continued)

*Primary Examiner* — Sean McGarry
(74) *Attorney, Agent, or Firm* — Medlen & Carroll, LLP

(57) ABSTRACT

Inappropriate activation of innate immune responses in nematode intestinal epithelial cells underlies the pathophysiology of some inflammatory disorders. Immunostimulatory xenobiotics are known to protect nematodes from bacterial infection (e.g., *Pseudomonas aeruginosa*). Conversely, these same xenobiotics are toxic to uninfected nematodes. These xenobiotics were subjected to a forward genetic screen in uninfected nematodes to identify nematode mutants that were resistant to the deleterious effects of these xenobiotics. These resistant nematode strains contained hypomorphic mutations in each of the known components of the p38 MAP kinase cassette (tir-1, nsy-1, sek-1 and pmk-1), demonstrating that hyperstimulation of p38 MAPK innate immune responses may be responsible for the induced toxicity. A second genetic screen using dominant activators of the p38 MAPK pathway identified a single allele that had a gain-of-function (gf) mutation in nsy-1, the MAP kinase kinase kinase that acts upstream of p38 MAPK pmk-1.

16 Claims, 22 Drawing Sheets

(56) References Cited

OTHER PUBLICATIONS

Irazoqui, J. E. et al. (2010) "Evolution of host innate defence: insights from Caenorhabditis elegans and primitive invertebrates," *Nature Reviews Immunology* 10, 47.
Jorgensen, E. M. et al. (2002) "The art and design of genetic screens: Caenorhabditis elegans," *Nature Reviews Genetics* 3, 356.
Jung, S. O. et al. (2005) "Surface plasmon resonance imaging-based protein arrays for high-throughput screening of protein-protein interaction inhibitors," *Proteomics* 5(17), 4427-4431.
Kamna, A. et al. (2008) "Positive and negative regulation of the *Drosophila* immune response," *BMB Reports* 41(4), 267-277.
Kay, B. K. et al. (1996) "High-throughput screening strategies to identify inhibitors of protein-protein interactions," *Molecular Diversity* 1(2), 139-140.
Kim, D. H. et al. (2002) "A Conserved p38 MAP Kinase Pathway in Caenorhabditis elegans Innate Immunity," *Science* 297(5581), 623.
Kim, D. H. et al. (2004) "Integration of *Caenorhabditis elegans* MAPK pathways mediating immunity and stress resistance by MED-1 MAPK kinase and VHP-1 MAPK phosphatase," *Proceedings of the National Academy of Sciences of the United States of America* 101(30), 10990.
Kyriakis, J. M. et al. (2012) "Mammalian MAPK Signal Transduction Pathways Activated by Stress and Inflammation: A 10-Year Update, " *Physiological Reviews* 92(2), 689-737.
Larkin, M. A. et al. (2007) "Clustal W and Clustal X version 2.0," *Bioinformatics* 23(21), 2947-2948.
Liberati, N. T. et al. (2004) "Requirement for a conserved Toll/interleukin-1 resistance domain protein in the *Caenorhabditis elegans* immune response," *Proceedings of the National Academy of Sciences of the United States of America* 101(17), 6593.
Medzhitov, R. et al. (2012) "Disease Tolerance as a Defense Strategy," *Science* (New York, N. Y.) 335(6071), 936-941.
Minevich, G. et al. (2012) "CloudMap: A Cloud-Based Pipeline for Analysis of Mutant Genome Sequences," *Genetics* 192(4), 1249.
Mizuno, T. et al. (2004) "The *Caenorhabditis elegans* MAPK phosphatase VHP-1 mediates a novel JNK-like signaling pathway in stress response," *EMBO Journal* 23(11), 2226.
Moy, T. I. et al. (2009) "High Throughput Screen for Novel Antimicrobials using a Whole Animal Infection Model," *ACS Chemical Biology* 4(7), 527-533.
Nieuwenhuijsen, B. W. et al. (2003) "A Dual Luciferase Multiplexed High-Throughput Screening Platform for Protein-Protein Interactions," *Journal of Biomolecular Screening* 8(6), 676-684.
Osmond, R. I. W. et al. (2005) "GPCR Screening via ERK 1/2: A Novel Platform for Screening G Protein-Coupled Receptors," *Journal of Biomolecular Screening* 10(7), 730-737.
Peterson, L. W. et al. (2014) "Intestinal epithelial cells: regulators of barrier function and immune homeostasis," *Nature Reviews Immunology* 14, 141.
Pfaffl, M. W. (2001) "A new mathematical model for relative quantification in real-time RT-PCR," *Nucleic Acids Research* 29(9), e45-e45.
Pfleger, K. D. G. et al. (2006) "Extended bioluminescence resonance energy transfer (eBRET) for monitoring prolonged protein—protein interactions in live cells," *Cellular Signalling* 18(10), 1664-1670.
Pukkila-Worley, R. et al. (2012) "Immune defense mechanisms in the Caenorhabditis elegans intestinal epithelium," *Current Opinion in Immunology* 24(1), 3-9.
Pukkila-Worley, R. et al. (2011) "*Candida albicans* Infection of *Caenorhabditis elegans* Induces Antifungal Immune Defenses," *PLoS Pathogens* 7(6), e1002074.
Pukkila-Worley, R. et al. (2012) "Stimulation of Host Immune Defenses by a Small Molecule Protects C. elegans from Bacterial Infection," *PLoS Genetics* 8(6), e1002733.
Pukkila-Worley, R. et al. (2014) "The Evolutionarily Conserved Mediator Subunit MDT-15/MED15 Links Protective Innate Immune Responses and Xenobiotic Detoxification," *PLoS Pathogens* 10(5), e1004143.
Pukkila-Worley, R. et al. (2014) "Case 28-2014," *New England Journal of Medicine* 371(11), 1051-1060.
Richardson, C. E. et al. (2010) "An essential role for XBP-1 in host protection against immune activation in C. elegans," *Nature* 463, 1092.
Sarin, S. et al. (2008) "Caenorhabditis elegans mutant allele identification by whole-genome sequencing," *Nature Methods* 5, 865.
Shivers, R. P. et al. (2009) "Tissue-Specific Activities of an Immune Signaling Module Regulate Physiological Responses to Pathogenic and Nutritional Bacteria in C. elegans," *Cell Host & Microbe* 6(4), 321-330.
Shivers, R. P. et al. (2010) "Phosphorylation of the Conserved Transcription Factor ATF-7 by PMK-1 p38 MAPK Regulates Innate Immunity in Caenorhabditis elegans," *PLoS Genetics* 6(4), e1000892.
Stockwell, B. R. (2004) "Exploring biology with small organic molecules," *Nature* 432, 846.
Sun, J. et al. (2011) "Neuronal GPCR Controls Innate Immunity by Regulating Noncanonical Unfolded Protein Response Genes, " *Science* 332(6030), 729.
Tan, M.-W. et al. (1999) "Killing of *Caenorhabditis elegans* by *Pseudomonas aeruginosa* used to model mammalian bacterial pathogenesis," *Proceedings of the National Academy of Sciences* 96(2), 715.
Timmons, L. et al. (2001) "Ingestion of bacterially expressed dsRNAs can produce specific and potent genetic interference in Caenorhabditis elegans," *Gene* 263(1), 103-112.
Troemel, E. R. et al. (2006) "p38 MAPK Regulates Expression of Immune Response Genes and Contributes to Longevity in C. elegans," *PLoS Genetics* 2(11), e183.
Visvikis, O. et al. (2014) "Innate Host Defense Requires TFEB-Mediated Transcription of Cytoprotective and Antimicrobial Genes," *Immunity* 40(6), 896-909.
Waetzig, G. H. et al. (2002) "p38 Mitogen-Activated Protein Kinase Is Activated and Linked to TNF-α Signaling in Inflammatory Bowel Disease," *Journal of Immunology* 168(10), 5342.
Xavier, R. J. et al. (2007) "Unravelling the pathogenesis of inflammatory bowel disease," *Nature* 448, 427.
Zhang, R. et al. (2012) "Tools for GPCR drug discovery," *Acta Pharmacologica Sinica* 33, 372.
PCT International Search Report of International Application No. PCT/US2017/013227 dated Mar. 31, 2017.

ANTIHELMINTHIC MEDICATIONS FOR PATHOGENIC NEMATODES

STATEMENT OF GOVERNMENTAL SUPPORT

This invention was made with government support K08 AI081747 awarded by NIH/NIAID. The government has certain rights in the invention.

FIELD OF THE INVENTION

The present invention is related to the treatment and prevention of nematode infection in mammals. For example, a G protein-coupled receptor OLRN-1 is a putative therapeutic target to treat human pathogenic nematode infections. In general, the present invention provides small molecules that trigger aberrant immune responses in human pathogenic nematodes as antihelminthic medications. Further, the present invention combines an immunostimulatory small molecule with a pharmacologic inducer of an endoplasmic reticulum unfolded protein response that provides a synergistic therapy for human pathogenic nematode infection.

BACKGROUND

Parasitic nematodes disproportionately affect the poorest individuals in the world. The soil-transmitted intestinal nematodes, *Ascaris lumbricoides*, hookworm (*Necator americanus* and *Ancylostoma duodenale*) and whipworm (*Trichuris trichiura*), have a staggering global burden: up to 1.5 billion people are chronically infected with one of these nematodes by some estimates. Infection often begins in childhood and can have myriad consequences that persist into adulthood. In children, these pathogens cause malnourishment, can stunt intellectual and physical growth, and have been directly linked to school absenteeism. Thus, these infectious diseases can have a profound impact on the economic stability of both individuals and communities.

Another major intestinal pathogenic nematode, *Strongyloides stercoralis*, has the unique ability to replicate inside the human host, and thus it can persist for decades via a process called autoinfection. Although accurate estimates are difficult to determine, as many as 500 million people may be infected with this pathogen, which is a particular problem in the setting of immune compromise when *Strongyloides* can cause overwhelming infection and death.

The filarial nematodes comprise a separate class of tissue-dwelling helminths that are be transmitted by the bite of an insect vector. This group includes the etiological agent of river blindness (*Onchocerca volvulus*), lymphatic filariasis (*Wucheria bancrofti* and *Brugia* sp.) and loiaisis (*Loa loa*), which together have an enormous socioeconomic impact in the developing world as the cause of preventable blindness and debilitating edema of the lower extremities and genitalia.

Despite repeated calls for action by the World Health Organization, these neglected tropical diseases remain a scourge of humanity. Preventative chemotherapy through mass treatment of susceptible populations is a possible solution to this public health crisis; however, no single agent is active against all pathogenic nematodes. For example, albendazole is the only currently available medication with an adequate efficacy and safety profile for single-dose mass administration. It is believed effective against *Ascaris*, but has variable activity against hookworm, and no activity against whipworm. In addition, albendazole is not efficacious enough toward *Strongyloides* and the filarial nematodes to enable single dose treatment.

What is urgently needed in the art are new pharmaceutical therapies that are capable of broad spectrum nematode clinical effectiveness.

SUMMARY OF THE INVENTION

The present invention is related to the treatment and prevention of nematode infection in mammals. For example, a G protein-coupled receptor OLRN-1 is a putative therapeutic target to treat human pathogenic nematode infections. In general, the present invention provides small molecules that trigger aberrant immune responses in human pathogenic nematodes as antihelminthic medications. Further, the present invention combines an immunostimulatory small molecule with a pharmacologic inducer of an endoplasmic reticulum unfolded protein response that provides a synergistic therapy for human pathogenic nematode infection.

In one embodiment, the present invention contemplates a pharmaceutical composition comprising a p38 mitogen activated protein kinase immune response pathway inducer and at least one excipient. In one embodiment, the p38 mitogen activated protein kinase immune response pathway inducer is a small organic compound. In one embodiment, the small organic compound is RPW-24 (hereinafter refered to as R24). In one embodiment, the p38 mitogen activated protein kinase immune response pathway inducer comprises a G protein coupled receptor RNAi molecule. In one embodiment, the G protein coupled receptor RNAi molecule is an OLRN-1 receptor RNAi molecule.

In one embodiment, the present invention contemplates a method, comprising: a) providing: i) a patient exhibiting at least one nematode infection symptom; ii) a nematode comprising a p38 mitogen activated protein kinase immune response pathway, wherein said nematode lacks a toxic bacterial infection; and iii) a p38 mitogen activated protein kinase immune response pathway inducer; b) administering said inducer to said patient; and c) reducing said at least one nematode infection symptom. In one embodiment, the p38 mitogen activated protein kinase immune response pathway inducer is a small organic compound. In one embodiment, the small organic compound is R24. In one embodiment, the p38 mitogen activated protein kinase immmune response pathway inducer is a cell surface G protein-coupled receptor RNAi molecule. In one embodiment, the cell surface G protein-coupled receptor RNAi molecule is an OLRN-1 receptor RNAi molecule. In one embodiment, the p38 mitogen activated protein kinase immune response pathway activates an immune response. In one embodiment, the p38 mitogen activated protein kinase immune response pathway inducer has specific affinity for a cell surface G protein-coupled receptor. In one embodiment, the cell surface G protein-coupled receptor is an OLRN-1 receptor. In one embodiment, the nematode is an adult nematode. In one embodiment, the nematode is selected from the group consisting of *C. elegans, Ascaris lumbricoides, Necator americanus, Ancylostoma duodenale, Trichuris trichiura, Strongyloides stercoralis, Onchocera, Wucheria bancrofti* and *Loa loa*.

In one embodiment, the present invention contemplates a method, comprising: a) providing: i) a patient comprising a plurality of nematodes, wherein said plurality of nematodes comprise a p38 mitogen activated protein kinase immune response pathway and lacks a toxic bacterial infection; and ii) a p38 mitogen activated protein kinase immune response pathway inducer; b) administering said inducer to said patient; c) hyperactivating said p38 mitogen activated protein kinase immune response pathway; and d) killing at least a portion of said nematodes. In one embodiment, the p38 mitogen activated protein kinase immune response pathway activates an immune response. In one embodiment, the p38 mitogen activated protein kinase immune response pathway inducer has specific affinity for a cell surface G protein-coupled receptors. In one embodiment, the cell surface G protein-coupled receptor is an OLRN-1 receptor. In one embodiment, the p38 mitogen activated protein kinase immune response pathway inducer is a small organic molecule. In one embodiment, the small organic molecule inhibitor is R24. In one embodiment, the p38 mitogen activated protein kinase immune response pathway inducer is a cell surface G protein-coupled receptor RNAi molecule. In one embodiment, the cell surface G protein-coupled receptor RNAi is an OLRN-1 receptor RNAi molecule. In one embodiment, the hyperactivating produces a nematode-toxic immune response. In one embodiment, the method further comprises inducing a nematode endoplasmic reticulum unfolded protein response following administration of the p38 pathway inducer. In one embodiment, the nematode is an adult nematode. In one embodiment, the nematode is selected from the group consisting of *C. elegans, Ascaris lumbricoides, Necator americanus, Ancylostoma duodenale, Trichuris trichiura, Strongyloides stercoralis, Onchocera, Wucheria bancrofti* and *Loa loa*.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" as used herein, in the context of any of any assay measurements refers to +/−5% of a given measurement.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

The term "suspected of having", as used herein, refers a medical condition or set of medical conditions (e.g., preliminary symptoms) exhibited by a patient that is insufficient to provide a differential diagnosis. Nonetheless, the exhibited condition(s) would justify further testing to obtain further information on which to base a diagnosis.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds that exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc.) to a binding partner under conditions such that the binding partner becomes unresponsive to its natural ligands. Inhibitory compounds may include, but are not limited to, small organic molecules, antibodies, and proteins/peptides.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal (e.g., for example, a mammal) and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the terms "siRNA" refers to either small interfering RNA, short interfering RNA, or silencing RNA. Generally, siRNA comprises a class of double-stranded RNA molecules, approximately 20-25 nucleotides in length. Most notably, siRNA is involved in RNA interference (RNAi) pathways and/or RNAi-related pathways. wherein the compounds interfere with gene expression.

As used herein, the term "shRNA" refers to any small hairpin RNA or short hairpin RNA. Although it is not necessary to understand the mechanism of an invention, it is believed that any sequence of RNA that makes a tight hairpin turn can be used to silence gene expression via RNA interference. Typically, shRNA uses a vector stably introduced into a cell genome and is constitutively expressed by a compatible promoter. The shRNA hairpin structure may also cleaved into siRNA, which may then become bound to the RNA-induced silencing complex (RISC). This complex binds to and cleaves mRNAs which match the siRNA that is bound to it. As used herein, the term "microRNA", "miRNA", or "μRNA" refers to any single-stranded RNA molecules of approximately 21-23 nucleotides in length, which regulate gene expression. miRNAs may be encoded by genes from whose DNA they are transcribed but miRNAs are not translated into protein (i.e. they are non-coding RNAs). Each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to downregulate gene expression.

A "variant" of a protein is defined as an amino acid sequence which differs by one or more amino acids from a polypeptide sequence or any homolog of the polypeptide sequence. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs including, but not limited to, DNAStar® software.

A "variant" of a nucleotide is defined as a novel nucleotide sequence which differs from a reference oligonucleotide by having deletions, insertions and substitutions. These may be detected using a variety of methods (e.g., sequencing, hybridization assays etc.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, for example, the naturally occurring sequences.

A "substitution" results from the replacement of one or more nucleotides or amino acids by different nucleotides or amino acids, respectively.

The terms "immunogen," "antigen," "immunogenic" and "antigenic" refer to any substance capable of generating antibodies when introduced into an animal. By definition, an immunogen must contain at least one epitope (the specific biochemical unit capable of causing an immune response), and generally contains many more. Proteins are most frequently used as immunogens, but lipid and nucleic acid moieties complexed with proteins may also act as immunogens. The latter complexes are often useful when smaller molecules with few epitopes do not stimulate a satisfactory immune response by themselves.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

BRIEF DESCRIPTION OF THE FIGURES

FIG. 2A: The chemical structure of R24.

FIG. 2B: Photomicrographs showing R24 inhibition of induced F08G5.6::GFP transgene expression.

FIG. 2C: Data showing the R24 dose-dependent improvement in *C. elegans* survival during a *P. aeruginosa* bacterial infection.

FIG. 2D: Data showing the lack of effect of R24 on an in vitro *P. aeruginosa* growth curve.

FIG. 3A: Improved survivability with R24 in wild-type *C. elegans*.

FIG. 3B: Lack of improved survivability with R24 in pmk-1(km25) null *C. elegans* mutants.

FIG. 4A: Exemplary results of a mutagenized haploid *C. elegans* genome screen for mutants that were able to develop in the presence of R24. Five alleles were identified and termed xenobiotic toxicity suppressors (e.g., an xts phenotype).

FIG. 4B: Exemplary results showing that exposure to R24 caused a dose dependent shortening of *C. elegans* survival.

FIG. 4C: Exemplary results showing that xbp-1(zc12) loss-of-function mutants were dramatically susceptible to the toxic effects of R24 in a development assay compared to wild-type controls.

FIG. 5A: RNAi knockdown of the expression of nsy-1 in the ums8 mutant suppressed F08G5.6::GFP induction. Green shows expressed F08G5.6::GFP. Red shows a co-injection marker.

FIG. 5B: A nanoString transcriptome profiling experiment showing that nys-1(ums8) drives the transcription of seven p38 MAPK-dependent immune effectors.

FIG. 5C: nsy-1(ums8) nematodes have greater amounts of activated p38 MAPK PMK-1 than control nematodes. Arrow on the right points to the p-PMK-1 band. Arrowheads indicate non-specific bands.

FIG. 5D: A human homolog of NSY-1, ASK1 comprising at least three conserved protein domains: a central serine-threonine kinase domain (red) and two coiled-coil domains in the N and C termini.

FIG. 6A: ORLN-1 receptor mutations cause constitutive F08G5.6::GFP expression. Green shows expressed F08G5.6::GFP. Red shows a co-injection marker.

FIG. 6B: A nanoString experiment showing elevation in p38 MAPK-dependent gene activity in olrn-1 loss-of-function mutants.

FIG. 6C: Nematodes with an olrn-1(ums9) mutant is more resistant to *P. aeruginosa* infection lethality.

FIG. 6D: olrn-1(ums9) nematode mutants have smaller brood sizes as compared to wild type nematodes. *P<0.05.

FIG. 9 presents exemplary data showing p38 MAPK mutants that have a Xenobiotic toxicity suppressor (Xts) phenotype.

FIG. 10 presents exemplary data showing that the nsy-1 (ums8) allele encodes a gain-of-function mutation in nsy-1.

FIG. 11 presents exemplary data showing that the nsy-1 (ums8) gain-of-function allele causes the induction of p38 MAPK dependent putative immune effectors in a manner that is synergistic with R24.

FIG. 12 presents exemplary data showing that RNAi-mediated knockdown of pmk-1 suppresses F08G5.6::GFP activation and the delayed development of the nsy-1(ums8) mutant.

FIG. 13 presents exemplary data showing that p38 MAPK-dependent putative immune effectors are constitutively activated in the nsy-1(ums8) mutant.

FIG. 14 presents exemplary data showing an endogenous hyperactivation of p38 MAPK innate immune responses that protects nematodes from bacterial infection and delays the development of wild-type nematodes. Wild-type nematodes were grown on RNAi bacteria expressing the empty vector L4440 (Wild-type) or a construct designed to knockdown nsy-1 [nsy-1(RNAi)]. nsy-1(ums8) animals were grown in parallel on RNAi bacteria expressing the empty vector L4440 [nsy-1(ums8)] or a construct designed to knockdown nsy-1 [nsy-1(ums8)+nsy-1(RNAi)].

DETAILED DESCRIPTION OF THE INVENTION

Figure 1:
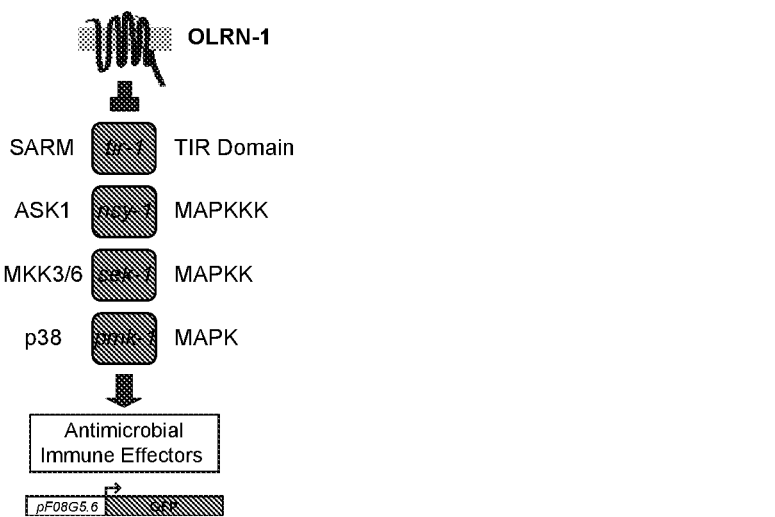
FIG. 1 presents an illustration of one embodiment of a nematode p38 MAPK pathway that produce antimicrobial immune effectors. Nematode proteins are listed on the right and their respective human orthologs are listed on the left.

The present invention is related to the treatment and prevention of nematode infection in mammals. For example, a G protein-coupled receptor OLRN-1 is a putative therapeutic target to treat human pathogenic nematode infections. In general, the present invention provides small molecules that trigger aberrant immune responses in human pathogenic nematodes as antihelminthic medications. Further, the present invention combines an immunostimulatory small molecule with a pharmacologic inducer of an endoplasmic reticulum unfolded protein response that provides a synergistic therapy for human pathogenic nematode infection.

In some embodiments, the present invention contemplates that small molecule-mediated hyperactivation of innate immune signaling in pathogenic nematodes is an effective treatment strategy for parasitic helminths infection in mammals. For example, a microscopic nematode *Caenorhabditis elegans* may be studied due to its evolutionarily conserved principals of pathogen detection and immune regulation. Pukkila-Worley et al., *Curr Opin Immunol* 24:3-9 (2012). Previous reports demonstrated that *C. elegans* can be used in pathogenesis assays to mine large chemical libraries for small molecules that stimulate host immune defenses against bacterial infections via a conserved p38 MAPK pathway. It was found that innate immune activation and xenobiotic detoxification programs are engaged simultaneously via a conserved transcriptional regulator. Pukkila-Worley et al., *PLoS Genet* 2012; 8:e1002733; and Pukkila-Worley et al., *PLoS Pathog* 2014; 10:e1004143. In one embodiment, the present invention contemplates a method of immune regulation in nematodes comprising hyperactivating an innate immune bacterial defense pathway that is toxic to an uninfected nematode (i.e., for example, *C. elegans*).

In one embodiment, the present invention contemplates a composition comprising an antihelminthic small molecule immune activator. Although it is not necessary to understand the mechanism of an invention, it is believed that small molecule-mediated hyperactivation of innate immune signaling mechanisms in pathogenic nematodes can provide a broad spectrum treatment for parasitic helminth infections. For example, it is believed that such small molecule immune activators are mediated via cell surface receptors that are conserved only in nematodes.

The data presented herein focuses on the p38 MAPK pathway in *C. elegans* and examines some physiological consequences of innate immune hyperactivation in nematode intestinal epithelial cells. From two different forward genetic screens, evidence is presented suggesting that aberrant activation of p38 MAPK-mediated defenses in nematode intestinal epithelial cells is actually deleterious to nematodes. Although it is not necessary to understand the mechanism of an invention, it is believed that such nematode toxicity associated with exogenous stimulation of the p38 MAPK-mediated immune responses can be suppressed through loss-of-function mutations in p38 MAPK pathway components. To validate this possible mechanism, a gain-of-function allele of MAPKKK nsy-1 was identified and characterized that drives hyperactivation of the p38 MAPK PMK-1 pathway. Accordingly, this nsy-1(gf) allele is believed protective against bacterial infection of the nematode, but this same concomitant hyperactivation of innate immune effectors is deleterious to uninfected nematodes. These data suggest that the MAPKKK NSY-1 is negatively regulated as a part of mechanism to ensure immune homeostasis.

The present invention has specific advantages over current treatment options for human pathogenic nematode infections. In developing a nematocidal therapy that targets a receptor common to all of the most clinically relevant pathogenic nematodes, such therapies can deworm large human populations regardless of the nematode species responsible for each individual's infection. In essence, the therapies contemplated herein are broad spectrum therapies. Hyperactivation of immune responses is toxic to adult nematodes, and thus these immunostimulatory treatments are superior to the most widely used antihelminthic medication, ivermectin, which can only kill nematode larvae for some species (e.g. *Onchocerca*). For this reason, several administrations of ivermectin are often needed to cure patients of infections with pathogenic helminths, whereas a clinically effective cure with the compositions contemplated herein can be achieved with a single administration.

I. Nematode Infections

Infections with soil-transmitted intestinal nematodes, in particular roundworm (*Ascaris lumbricoides*), hookworm (*Necator americanus* and *Ancylostoma duodenale*) and whipworm (*Trichuris trichiura*), are nearly ubiquitous in the developing world. These pathogens often infect children early in life and can stunt intellectual and physical growth, prevent school attendance, and have a profoundly negative impact on socioeconomic stability, thus trapping individuals and communities in cycles of poverty, malnourishment and disease. Another major intestinal pathogenic nematode, *Strongyloides stercoralis* can persist for decades in a human host and cause overwhelming infection and death in the setting of immune compromise. Pukkila-Worley et al., *N Engl J Med* 371:1051-1060 (2014). The tissue-dwelling or filarial nematodes, such as *Onchocera, Wucheria bancrofti* and *Loa loa*, comprise a second major group of human parasitic nematodes and include the etiologic agents of elephantiasis (debilitating edema of the lower extremity and genitals) and river blindness, a major cause of preventable sight loss in the developing world.

Coordination of innate immune responses at mucosal surfaces may be a determinant of cellular homeostasis in evolutionarily diverse organisms. Peterson et al., "Intestinal epithelial cells: regulators of barrier function and immune homeostasis" *Nat Rev Immunol* 14:141-153 (2014). Exaggerated or aberrantly triggered immune responses, for example, underlie the pathophysiology of inflammatory disorders of the human intestine. Xavier et al., "Unravelling the pathogenesis of inflammatory bowel disease" *Nature* 448:427-434 (2007). In flies, immune pathway hyperactivation also has negative physiological consequences and is subject to feedback control. Aggarwal et al., "Positive and negative regulation of the *Drosophila* immune response" *BMB Rep* 41: 267-277 (2008).

To understand ancient mechanisms of pathogen detection and immune regulation, the innate immune responses in nematodes (e.g., *C. elegans*) have been examined. Irazoqui et al., "Evolution of host innate defence: insights from *Caenorhabditis elegans* and primitive invertebrates" *Nat Rev Immunol* 10: 47-58 (2010); Pukkila-Worley et al., "Immune defense mechanisms in the *Caenorhabditis elegans* intestinal epithelium" *Curr. Opin. Immunol.* 24:3-9 (2012); and Cohen et al., "Microbial pathogenesis and host defense in the nematode *C. elegans*" *Curr Opin Microbiol* 23:94-10 (2015). As in other metazoans, nematodes coordinate inducible immune defenses from intestinal epithelial cells (IECs), which provide a barrier against ingested pathogens. Kim et al., "A conserved p38 MAP kinase pathway in *Caenorhabditis elegans* innate immunity" *Science* 297:623-626 (2002); Shivers et al., "Tissue-Specific Activities of an Immune Signaling Module Regulate Physiological Responses to Pathogenic and Nutritional Bacteria in *C. elegans*" *Cell Host Microbe* 6:321-330 (2009); and Pukkila-Worley et al., "*Candida albicans* infection of *Caenorhabditis elegans* induces antifungal immune defenses" *PLoS Pathog.* 7:e1002074 (2011). Studies from *C. elegans* and other diverse organisms have revealed that innate immune signaling regulators may be strongly conserved. Irazoqui et al., "Evolution of host innate defence: insights from *Caenorhabditis elegans* and primitive invertebrates" *Nat Rev Immunol* 10: 47-58 (2010); Pukkila-Worley et al., "Immune defense mechanisms in the *Caenorhabditis elegans* intestinal epithelium" *Curr. Opin. Immunol.* 24:3-9 (2012); and Visvikis et al., "Innate host defense requires TFEB-mediated transcription of cytoprotective and antimicrobial genes" *Immunity* 40:896-909 (2014). For example, the NSY-1-SEK-1-PMK-1 Mitogen Activated Protein Kinase (MAPK) pathway in *C. elegans*, which is orthologous to the mammalian ASK1-MKK3/6-p38 MAPK pathway, controls the induction of putative antimicrobial immune effectors and may play a role in nematode intestinal epithelial cells to survive challenges from ingested pathogens.

In mammals, the ASK1-MKK3/6-p38 signaling cassette is believed to be a central regulator of inflammatory cytokine production in response to pathogen detection at epithelial surfaces, and pathway activation is tightly regulated through negative regulatory circuits. Misregulation of p38 signaling in IECs has been implicated in the pathogenesis of inflammatory bowel disease, cancer, autoimmune disorders and immunodeficiency syndromes. Waetzig et al., "p38 Mitogen-Activated Protein Kinase Is Activated and Linked to TNF-α Signaling in Inflammatory Bowel Disease" *J Immunol* 168:5342-5351 (2002); and Kyriakis et al., "Mammalian MAPK signal transduction pathways activated by stress and inflammation: a 10-year update" *Physiol. Rev.* 92:689-737 (2012). From an evolutionary perspective, it is therefore logical that mechanisms of immune homeostasis are selected for as part of a survival strategy, particularly for organisms such as bacterivorous nematodes that live in microbe-rich environments and may distinguish pathogens from potential food sources.

II. Nematode Immunology

In nature, nematodes consume bacteria for food and have evolved innate immune mechanisms within their intestinal epithelium to defend against ingested pathogens. Pukkila-Worley and Ausubel, (2012). For example, these regulators include, but are not limited to, the NSY-1/SEK-1/PMK-1 Mitogen Activated Protein (MAP) kinase pathway which may be orthologous to the ASK1 (MAP kinase kinase kinase)/MKK3/6 (MAP kinase kinase)/p38 (MAP kinase) pathway in mammals. This nematode MAP pathway is strongly conserved throughout evolution. Unlike mammals, the nematode MAP pathway has a single toll-like receptor homolog, tol-1, that does not activate p38 MAPK signaling and does not play a role in pathogen detection. Kim et al., (2002); and Pukkila-Worley et al., *Curr Opin Immunol* 24:3-9 (2012); See, FIG. 1.

In *C. elegans*, the p38 MAP kinase pathway may act autonomously in the intestine to coordinate the expression of immune effectors such as C-type lectins and genes that encode antimicrobial peptides, which can be secreted into an intestinal lumen and are induced 10 to 100 fold in the presence of pathogens.

One nematode, *Caenorhabditis elegans*, has been reported regarding study of evolutionarily conserved principles of pathogen detection and immune regulation. Pukkila-Worley and Ausubel, (2012). For example, it has been demonstrated that *C. elegans* can be infected with pathogenic fungi, mount targeted immune responses towards fungal pathogens involving the conserved p38 MAPK immune pathway and can be used in pathogenesis assays to mine large chemical libraries for small molecules that stimulate host immune defenses. Innate immune and xenobiotic detoxification programs appear to be engaged simultaneously via a conserved transcriptional regulator. Pukkila-Worley et al., (2009b); Pukkila-Worley et al., (2011); (Pukkila-Worley et al., (2012); and Pukkila-Worley et al. (2014a).

In one embodiment, the present invention contemplates that a pathogen defense system within nematodes is based upon a hyperactivation of innate immune defenses by treatment with a small molecule immune stimulators or genetically through a gain-of-function mutation in a p38 MAPK pathway component that is toxic to nematodes (e.g., *C. elegans*).

III. Nematode-Specific Immunological Hyperactivation

A. Nematode Immune Response Negative Regulator Proteins

In one embodiment, the present invention contemplates a method of inhibiting nematode immune response negative regulator proteins with small molecules. It is believed that such nematode immune response negative regulator proteins provide potential new targets for nematocidal therapies for human pathogenic helminths.

Although it is not necessary to understand the mechanism of an invention, it is believed that small molecule nematode immune response negative regulator protein inhibitors act on immune regulatory protein pathways that are not conserved in humans. For example, in mammals, the p38 pathway is activated by Toll-like receptors, which recognize conserved microbial components. There is one Toll-like Receptor homolog in *C. elegans*, tol-1, but this receptor does not play a role in nematode pathogen detection. Pukkila-Worley and Ausubel, (2012).

The data shown herein identifies a small molecule that aberrantly triggers an immune response in *C. elegans* that is lethal to nematodes. In one embodiment, a nematode immune response negative regulator protein includes, but is not limited to, a cell surface G protein-coupled receptor. In one embodiment, the cell surface G protein-coupled receptor is olrn-1. Although it is not necessary to understand the mechanism of an invention, it is believed that the olrn-1 cell surface G protein coupled receptor is common to many clinically relevant pathogenic nematodes. In one embodiment, these pathogenic nematodes include, but are not limited to, *A. lumbricoides, N. americanus, A. duodenale, T. trichiura, S. stercoralis, O. volvulus, W bancrofti, B.* sp. and *L. loa*.

1. Nematode Protection Against Bacterial Infection

Bacterial pathogenesis assays in *C. elegans* can be used to mine large chemical libraries for novel anti-infective small molecules. For example, using this system, one hundred nineteen (119) small molecules were identified out of thirty-seven thousand two hundred fourteen (37,214) tested that prolonged the lifespan of nematodes infected with bacterial pathogens. Moy et al., (2009); and Pukkila-Worley et al., (2012). Because these bacterial screening platforms utilize live nematodes (*C. elegans*), it is believed that a subset small molecules identified in these types of screens might confer a survival advantage to bacterially infected nematodes by stimulating a nematode immune response. Supporting this hypothesis, thirty-one (31) small molecules of the one hundred nineteen (119) small molecules reported above did not have any structural relationship to known antimicrobials and ten (10) of these thirty-one (31) were effective in protecting *C. elegans* from bacterial infection at doses that did not inhibit growth of the pathogen in an in vitro growth assay.

Figure 2:
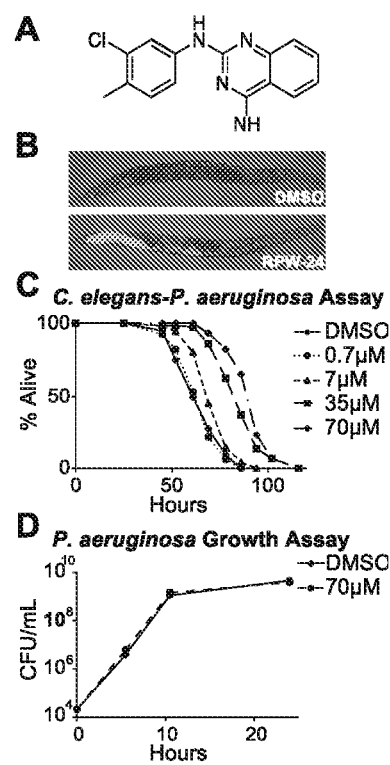
FIG. 2 presents exemplary data showing the effects of R24 on the bacteria *P. aeruginosa* infection of the nematode *C. elegans*.

The data presented herein determines whether any of these *C. elegans* bacterially protective compounds had immunostimulatory properties in uninfected nematodes. The studies utilized a GFP-based transcriptional reporter for F08G5.6, a *C. elegans* immune effector, that may be activated by several bacterial pathogens in a p38 MAPK PMK-1 pathway-dependent manner. Pukkila-Worley et al., (2012); Pukkila-Worley et al. (2014a). In particular, one screened compound, R24, strongly induced F08G5.6::GFP transgene expression. FIG. 2A and FIG. 2B. Further study showed that R24 protects *C. elegans* from a bacterial infection with gram-negative human pathogen *P. aeruginosa* in a dose-dependent manner. FIG. 2C. However, R24 did not have any effect on the growth of *P. aeruginosa* in an in vitro assay conducted in the absence of *C. elegans*. FIG. 2D.

The effects of R24 on *C. elegans* was further characterized by generating transcriptome profiles of wild-type nematodes following exposure to either 70 μM R24 or the solvent control DMSO using Affymetrix whole genome genechips. R24 induced a remarkably robust transcriptional response that involved only a small fraction (~1.3%) of the genes of the *C. elegans* genome. For example, two hundred sixty-nine (269) genes were upregulated three-fold or greater (P<0.025), one hundred twenty-five (125) of which were induced more than 50-fold during R24 exposure. Further, many of these upregulated genes were previously shown to be involved in the *C. elegans* transcriptional response to pathogenic bacteria. For example, seventy (70) of the two hundred sixty-nine (269) R24-induced genes were activated during infection with *P. aeruginosa* using a previously described gene set. Troemel et al., (2006). These data demonstrate an overlap that is greater than what would be expected by chance alone (P<$2.7\times10^{-16}$).

Figure 3:
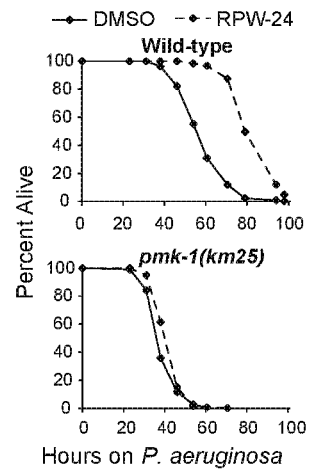
FIG. 3 presents exemplary data showing the effect of R24 on a specific p38 MAP kinase PMK-1 pathway protein loss-of-function mutant in *P. aeruginosa*-infected *C. elegans*.

Because R24 caused an induction of genes normally upregulated during bacterial infection, *C. elegans* immune gene activation by R24 may play a role in anti-infective activity. Using loss-of-function mutants for proteins in the p38 MAP kinase PMK-1 pathway (the central immune regulator in *C. elegans*) R24 efficacy in attenuating *P. aeruginosa*-mediated killing was determined. Indeed, the magnitude of R24-mediated lifespan prolongation of pmk-1(km25) null mutants infected with *P. aeruginosa* was significantly decreased compared to the lifespan extension observed in compound-treated wild-type nematodes. FIG. 3; P<0.001.

Using qRT-PCR, pmk-1(km25) mutants failed to upregulate six of ten antimicrobial immune effectors induced by R24 in wild-type nematodes following exposure to this small molecule. Four other known protein components of the p38 MAP kinase pathway were also tested (data not shown). As with the pmk-1(km25) mutant, the ability of R24 to prolong the lifespan of *C. elegans* with mutations in each of these p38 MAP kinase pathway protein signaling components was dramatically attenuated. Together, these data indicate that R24 robustly stimulates p38 MAP kinase-regulated defense responses to confer nematode protection from bacterial infection.

2. Nematode Toxicity From Autoimmune Hyperactivation

Figure 4:
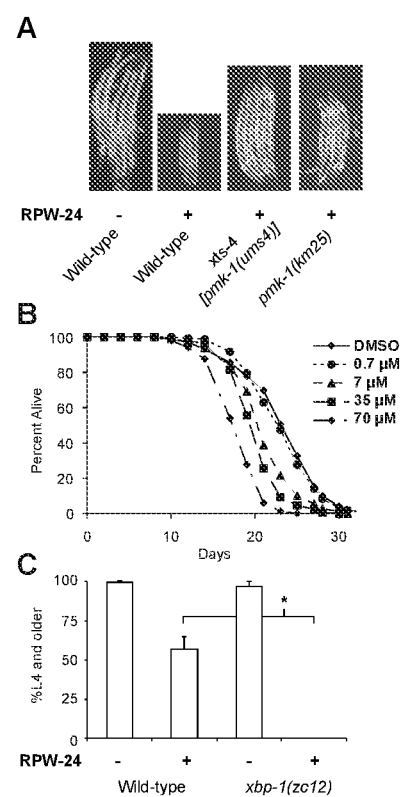
FIG. 4 presents exemplary data showing reduced growth and fertility of *C. elegans* in the presence of R24.

In reports describing the anti-infective, immunostimulatory xenobiotic R24 it was noted that this compound was toxic to nematodes growing in the absence of pathogen. Pukkila-Worley et al., (2012). Specifically, when nematodes were exposed to R24 from the first larval stage, their growth was markedly delayed compared to controls and their brood sizes were dramatically smaller. FIG. 4A. In addition, exposure to R24 caused a dose dependent shortening of *C. elegans* survival. FIG. 4B.

To investigate a possible connection between this toxicity and immunostimulatory properties of R24, a classical "forward" genetic screen for *C. elegans* mutants that are resistant to the toxic effects of the compound was performed. One hundred thousand (100,000) mutagenized haploid *C. elegans* genomes were screened for mutants that were able to develop in the presence of R24. Five alleles were identified which were termed xenobiotic toxicity suppressors (e.g., an xts phenotype). FIG. 4A. To identify the causative mutations in each of these xts strains, these mutant genomes were sequenced using Illumina's Next Generation Sequencing technology. Each of these five xts mutants contained missense mutations in one of the four known protein components of the p38 MAPK signaling cassette (i.e., for example, tir-1, nsy-1, sek-1 or pmk-1).

To characterize these newly-isolated p38 MAPK pathway mutants, pathogenesis assays were conducted with *P. aeruginosa* and found that, as with the classic loss-of-function mutants in p38 MAPK pathway protein components, the xts alleles were hypersusceptible to killing by *P. aeruginosa*. These xts mutants also had a reduction in the amount of activated PMK-1, as detected in an immunoblot experiment using an antibody that specifically recognizes the doubly phosphorylated TGY motif of PMK-1.

Together, these data demonstrate that the toxicity of R24 can be suppressed by hypomorphic mutations in the p38 MAPK pathway. Evaluation of previously reported classic loss-of-function alleles tir-1(qd4), nsy-1(ag3) and pmk-1 (km25) confirmed these observations where it was found that these mutations also suppressed the R24-induced developmental delay to a degree comparable to pmk-1(ums4) mutant, tir-1(ums2) tir-1(ums3) alleles, and pmk-1(km25). Kim et al., (2002); Shivers et al., (2009); and FIG. 4A.

R24 acts upstream of the p38 MAPK pathway to cause the induction of putative antibacterial immune effectors in the intestine of *C. elegans* and, accordingly, protects nematodes from bacterial infection. In addition, exposure to R24 causes the induction of detoxification enzymes and delays the development of wild-type nematodes in the absence of pathogen, suggesting that this compound is toxic to *C. elegans* under normal laboratory growth conditions. Pukkila-Worley et al., "The evolutionarily conserved mediator subunit MDT-15/MED15 links protective innate immune responses and xenobiotic detoxification" *PLoS Pathog.* 10:e1004143 (2014).

Figure 9A:
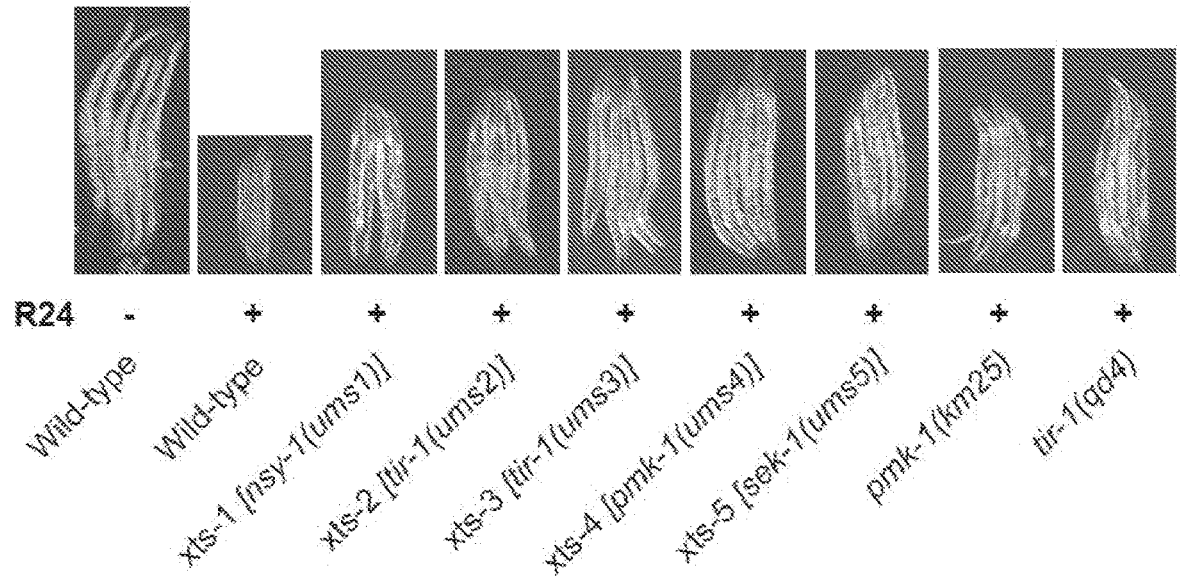
FIG. 9(A): Representative images of *C. elegans* mutants with an Xts phenotype photographed after three days of development at 20° C. in the presence (+) or absence (−) of 140 μM R24. *C. elegans* N2 animals were used as the wild-type control strain.
Figure 9B:
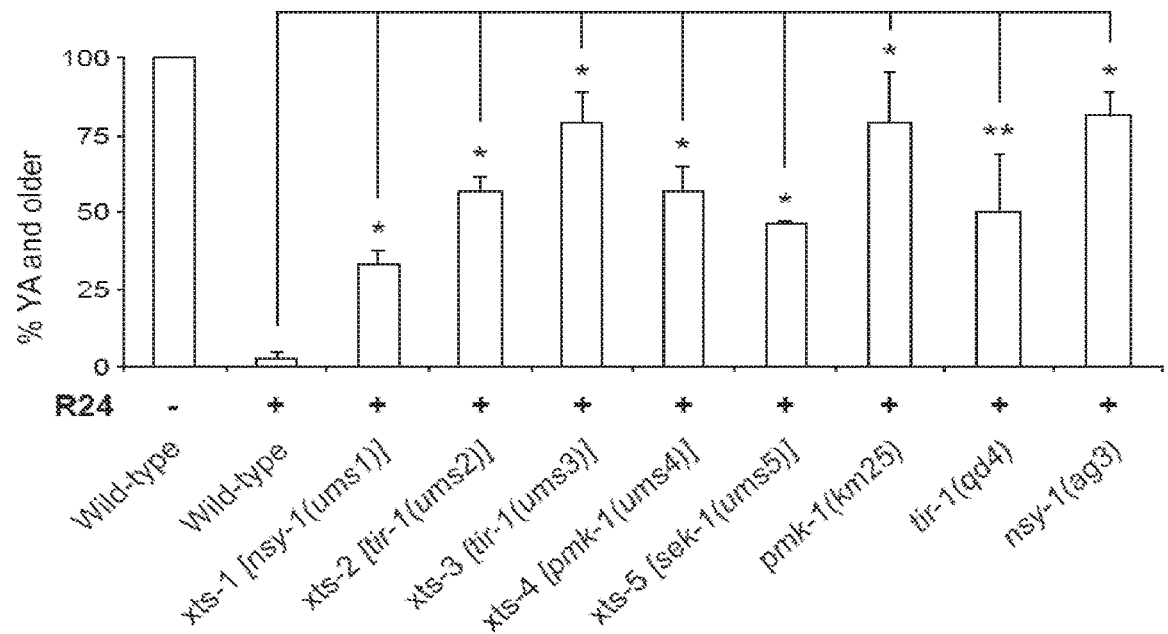
FIG. 9(B): Quantification of the percentage of nematodes that grew from the L1 to young adult (YA) stage for the experiment shown in FIG. 9A. Data are the average of two technical replicates with error bars giving the standard deviation between plates. The sample sizes for this experiment are: N2 (196), xts-1 [nsy-1(ums1)] (171), xts-2 [tir-1(ums2)] (193), xts-3 [tir-1(ums3)] (220), xts-4 [pmk-1(ums4)] (145), xts-5 [sek-1(ums5)] (196), pmk-1(km25) (155), tir-1(qd4) (269) and nsy-1 (ag3) (193). *p<0.05 **p=0.07 The data are representative of multiple biological replicate experiments, which were conducted during the backcrossing of the xts nematode mutants to wild-type nematodes.

To investigate the relationship between the immunostimulatory properties and the toxicity of this anti-infective xenobiotic, nematodes derived from approximately one hundred thousand (100,000) mutagenized haploid genomes were screened for mutants that were able to develop faster in the presence of 140 μM R24. For this screen, the selected nematode mutants were L4 larval stage or older at a time point when 100% of unmutagenized nematodes treated with R24 in parallel were at the L2 or L3 larval stage. Seven nematode mutants with xenobiotic toxicity suppressor (Xts) phenotypes were identified whereas five of these seven nematode mutants had most penetrant Xts phenotypes. FIGS. 9A and 9B.

To identify the mutation in these strains that permitted improved development in the presence of R24, next-generation sequencing technology was used. Sarin et al., "*Caenorhabditis elegans* mutant allele identification by whole-genome sequencing". *Nat. Methods* 5:865-867 (2008); and Minevich et al., "CloudMap: a cloud-based pipeline for analysis of mutant genome sequences" *Genetics* 192:1249-1269(2012). For three mutants (ums3, ums4 and ums5), DNA was sequenced from pooled F2 recombinants that had the mutant phenotype following a backcross to wild-type N2 animals. For two other mutants (ums1 and ums2), the mutations were identified after sequencing the original mutant strain. These five xts phenotype mutants each contained missense mutations in one of the four known components of the p38 MAPK signaling cassette (i.e., for example, tir-1, nsy-1, sek-1 or pmk-1). See, Table 1.

TABLE 1

Xenobiotic toxicity suppressors.

| Gene | Allele | Mutation | Strain | Description, Mammalian Ortholog |
|---|---|---|---|---|
| tir-1 | ums2 | L730F | xts-2 | TIR domain adaptor protein, SARM |
| tir-1 | ums3 | A723T | xts-3 | TIR domain adaptor protein, SARM |
| nsy-1 | ums1 | P874L | xts-1 | MAPKKK, ASK1 |
| sek-1 | ums5 | G199S | xts-5 | MAPKK, MKK3/6 |
| pmk-1 | ums4 | L296F | xts-4 | MAPK, p38 |

Table 1 presents a list of isolates identified in a screen for mutants that are able to develop faster in the presence of the immunostimulatory anti-infective xenobiotic R24 compared to controls.

Figure 9C:
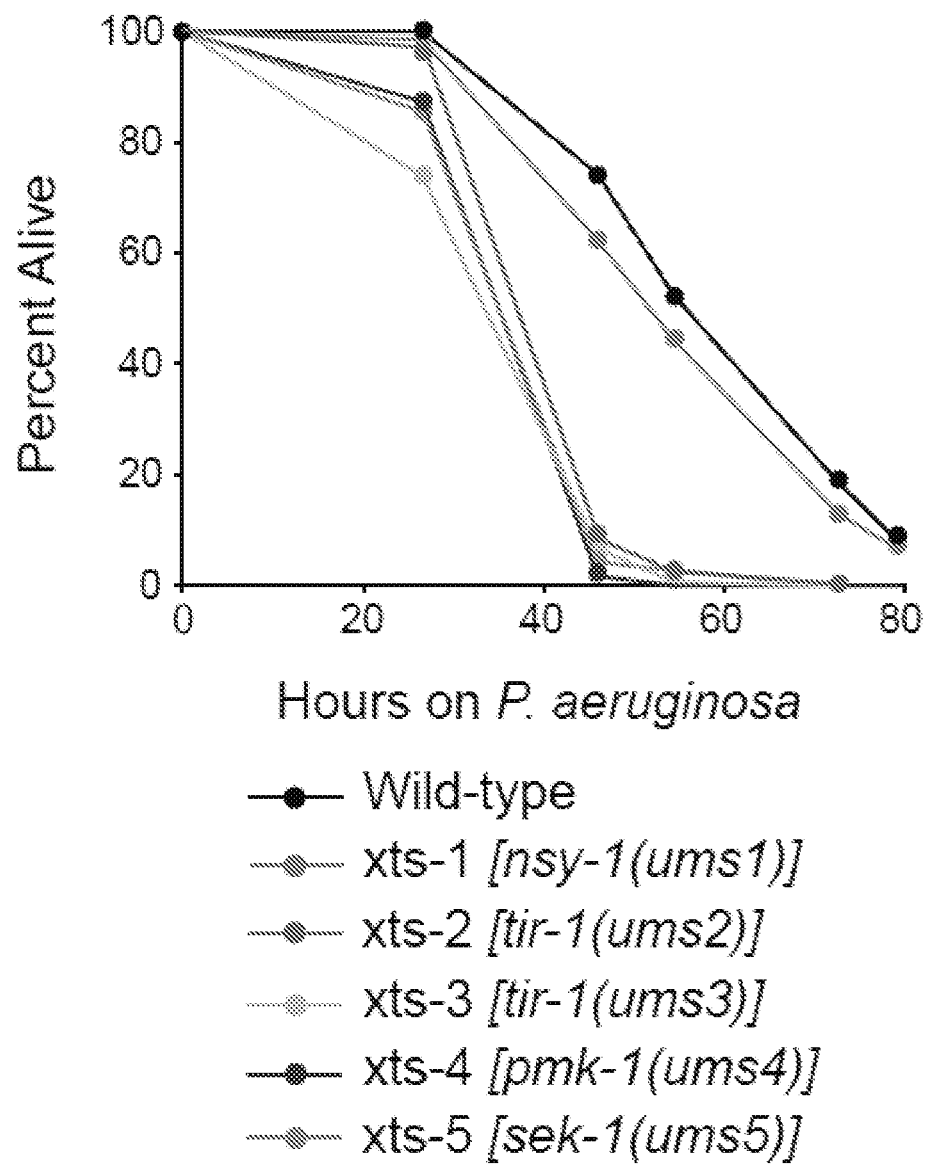
FIG. 9(C): A *P. aeruginosa* pathogenesis assay with *C. elegans* wild-type N2 and nematode mutants with an Xts phenotype is shown. The difference in *P. aeruginosa* susceptibility between all nematode mutants with an Xts phenotype and wild-type nematodes is significant ($p<0.001$), except xts-1 [nsy-1(ums1)] (p=n.s.). Sample sizes are: wild-type N2 (152), xts-1 [nsy-1(ums1)] (140), xts-2 [tir-1(ums2)] (151), xts-3 [tir-1(ums3)] (150), xts-4 [pmk-1(ums4)] (124) and xts-5 [sek-1(ums5)] (139).

To characterize these newly-isolated p38 MAPK pathway mutants, pathogenesis assays were conducted with *P. aeruginosa*. The data show that, as with the classic loss-of-function mutants in p38 MAPK pathway components, four of the five xts mutants (tir-1(ums2), tir-1(ums3), pmk-1 (ums4) and sek-1(ums5)) had an enhanced susceptibility to pathogens (Esp) phenotype (p<0.001). FIG. 9C. nsy-1 (ums1), the weakest toxicity suppressor of these five mutants, did not have an obvious Esp phenotype. In addition to conferring an Esp phenotype, loss- and reduction-of-function mutations in upstream components of the p38 MAPK PMK-1 pathway cause a reduction in the amount of activated PMK-1, which can be detected in an immunoblot experiment using an antibody that specifically recognizes the doubly phosphorylated TGY motif of PMK-1. Liberati et al., "Requirement for a conserved Toll/interleukin-1 resistance domain protein in the *Caenorhabditis elegans* immune response" *Proc Natl Acad Sci USA* 101 6593-6598 (2004).

Figure 9D:
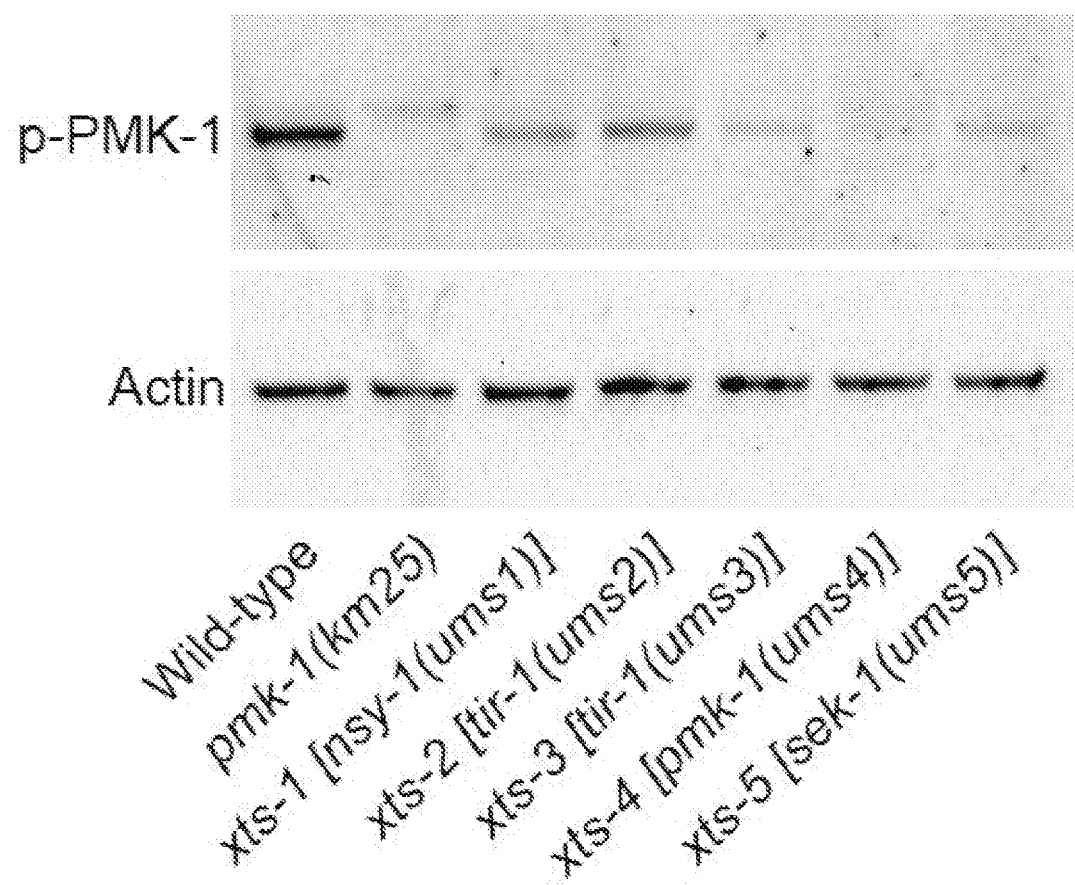
FIG. 9D: Immunoblot analysis of lysates from L4 larval stage nematodes of the indicated genotype using antibodies that recognize the doubly phosphorylated TGY motif of PMK-1 (p-PMK-1) and actin.

Each of the xts phenotype alleles had reduced levels of the active form of PMK-1 compared to wild-type controls. FIG. 9D. These data indicate that forward genetic screens for mutations that confer resistance to the toxic effects of the immunostimulatory xenobiotic R24 identified hypomorphic alleles in the p38 MAPK pathway. A previous forward genetic screen for loss-of-function mutations in the p38 MAPK pathway components identified two alleles, pmk-1 (qd9) and sek-1(qd37), which had the identical missense mutation as pmk-1(ums4) and at the same amino acid as sek-1(ums5), respectively. Shivers et al., "Phosphorylation of the conserved transcription factor ATF-7 by PMK-1 p38 MAPK regulates innate immunity in *Caenorhabditis elegans*" *PLoS Genet.* 6:e1000892 (2010).

Together, these data demonstrate that the toxicity of R24 can be suppressed by hypomorphic nematode mutations in the p38 MAPK pathway, although no single mutation was identified that resulted in growth progression identical to nematodes in the absence of R24. To confirm this observation, previously characterized null alleles tir-1(qd4), nsy-1 (ag3) and pmk-1(km25) were studied. These data showed that these mutations also suppressed the R24-induced developmental delay to a degree comparable to pmk-1(ums4) mutant, and the tir-1(ums2) and tir-1(ums3) alleles, respectively. FIGS. 9A and 9B. In summary, these data indicate that hyperactivation of p38 MAPK immune defenses is toxic to developing nematodes.

B. Unfolded Protein Response in Nematode Endoplasmic Reticulum

In one embodiment, the present invention contemplates a method comprising administering small molecules having clinical antihelminthic efficacy by inducing an unfolded protein response (UPR) in endoplasmic reticulum. In one embodiment, the unfolded endoplasmic reticulum protein response is mediated by small molecules including, but not limited to, tunicamycin and bortezomib (Velcade®). Tunicamycin and bortezomib are shown herein to act synergistically with immunostimulatory molecules to kill nematodes. See, FIG. 4C. Although it is not necessary to understand the mechanism of an invention, it is believed that components of the nematode UPR are strongly conserved and thus UPR inducers will have dose-limiting toxicity in mammals. Further, it is contemplated that lower, less toxic doses of these UPR inducers may also demonstrate synergy with immunostimulatory antihelminthic compounds disclosed herein.

During bacterial infection, C. elegans induces the transcription of over three hundred (300) genes, roughly half of which are trafficked through the endoplasmic reticulum (ER). Troemel et al., (2006). Indeed, C. elegans infection of intestinal epithelial cells represents a source of physiological stress that may result in a compensatory activity of the so-called unfolded protein response (UPR) to maintain homeostasis in the setting of the robust transcriptional response to pathogen challenge. Pukkila-Worley and Ausubel, (2012); Richardson et al., (2010); and Sun et al., (2011).

The data shown herein determines whether toxicity associated with the aberrant activation of innate immune mechanisms by R24 was caused by ER stress associated with an overwhelming of the UPR. In one pathway, the X box binding protein 1 (XBP-1) is believed to control a strongly conserved branch of the UPR. xbp-1(zc12) loss-of-function mutants were shown to be dramatically susceptible to the toxic effects of R24 in a development assay compared to wild-type controls, indicating that this gene may play a role in UPR when mediating R24-induced cellular toxicity. FIG. 4C.

In summary, these data demonstrate that small molecule-mediated hyperactivation of p38 MAPK-mediated innate immune defenses is toxic to nematodes at least in part through its effects on overwhelming the protein-folding capacity of the ER.

C. Gene Expression Regulation of Immune Response Negative Regulator Proteins

In one embodiment, the present invention contemplates a loss-of-function mutation in the olrn-1 gene. In one embodiment, the present invention contemplates an RNAi-mediated knockdown of olrn-1 gene expression. Although it is not necessary to understand the mechanism of an invention, it is believed that either a loss-of-function mutation or RNAi-mediated knockdown reduces olrn-1 gene expression such that an aberrant nematode immune response results in toxicity and/or is lethal to the nematode, and not the host organism.

Although it is not necessary to understand the mechanism of an invention, it is believed that because an exogenous stimulation of immune responses is toxic to nematodes, innate immune defenses in nematodes are physiologically regulated as a part of a mechanism to ensure cellular homeostasis. It is further believed that such endogenous regulators of host immune responses may be potential targets for new antihelminthic compounds.

1. Autoimmune Genetic Mutations that are Toxic to Nematodes

Figure 7:
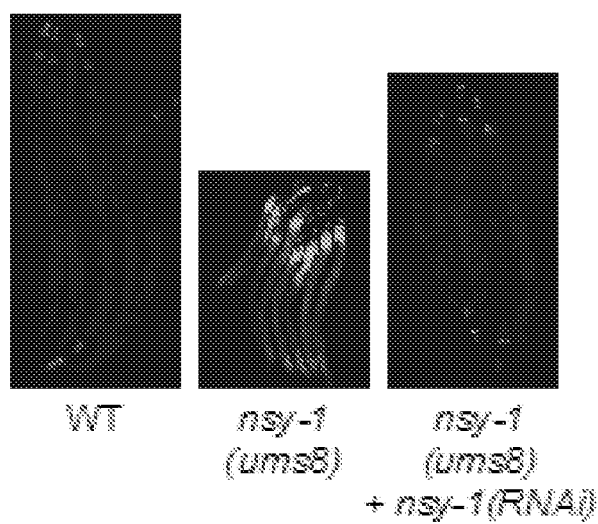
FIG. 7 presents exemplary data showing the results of a screen of mutagenized *C. elegans* that identified four mutants that caused constitutive F08G5.6::GFP expression

To identify the mechanisms of C. elegans immune regulation in an unbiased manner, a forward genetic screen was designed using F08G5.6::GFP, the transcriptional reporter that is an in vivo sensor of p38 MAPK pathway activation. Pukkila-Worley et al., (2012); and Pukkila-Worley et al. (2014a). A saturated screen of mutagenized C. elegans was performed that identified four mutants that caused constitutive F08G5.6::GFP expression. FIG. 7. Whole genome sequencing revealed that one of these mutants, ums8, contains a mutation (R246Q) in nsy-1/ASK1, the MAPPKKK upstream of p38 MAPK [nsy-1(ums8).

Figure 5:
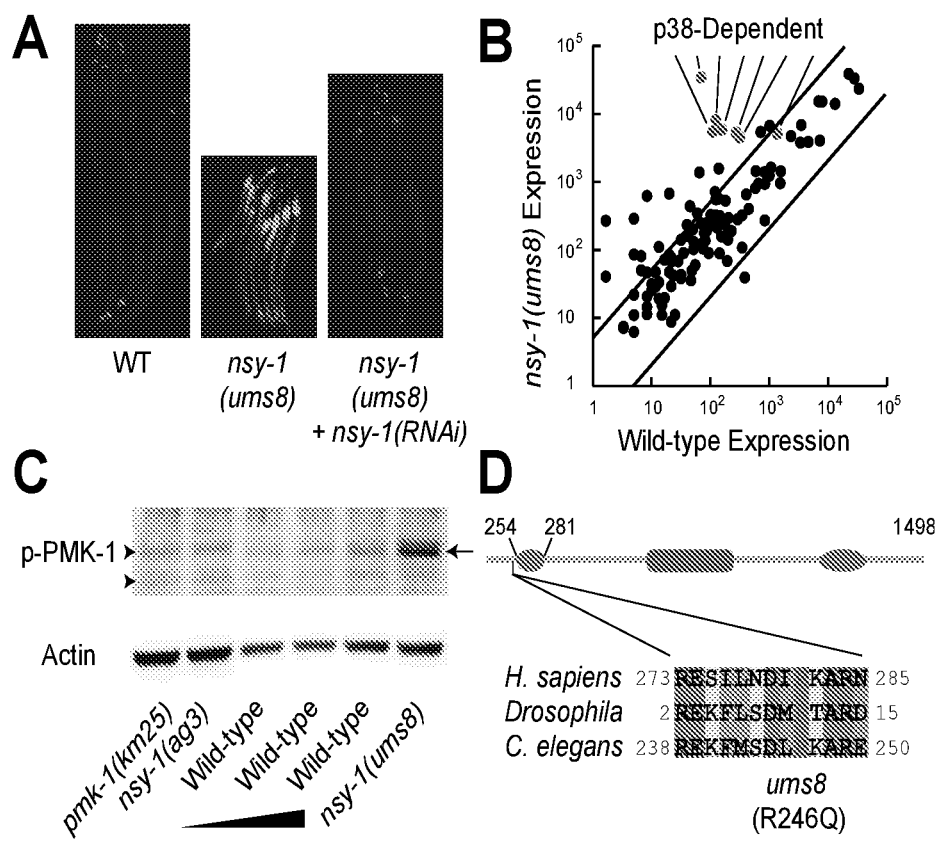
FIG. 5 presents exemplary data showing loss-of-function mutations in nematode genomes confer a self-toxic (autoimmune) immune response.

One hundred seventy thousand (170,000) mutagenized haploid C. elegans genomes were screened where four mutants were identified that caused constitutive F08G5.6::GFP expression. FIG. 5A. Whole genome sequencing revealed that one of these mutants, ums8, contains a dominant mutation (R246Q) in nsy-1/ASK1, the MAPPKKK protein located upstream of p38 MAPK [nys-1(ums8). FIGS. 1 and 5. To determine if the constitutive expression of the immune reporter F08G5.6::GFP in the ums8 mutant is caused by this missense mutation in nsy-1, an RNAi was used to knockdown the expression of nsy-1 in the ums8 mutant and found that this treatment suppressed F08G5.6::GFP induction, indicating that nsy-1(ums8) encodes a gain-of-function allele. FIG. 5A. Consistent with this observation, a nanoString transcriptome profiling experiment of one hundred eighteen (118) immune and stress response genes found that nys-1(ums8) drives the transcription of all seven p38 MAPK-dependent immune effectors that were in the codeset. FIG. 5B. Additionally, the nsy-1(ums8) nematodes had greater amounts of activated p38 MAPK PMK-1 than control nematodes in an immunoblot experiment. FIG. 5C.

Figure 13A:
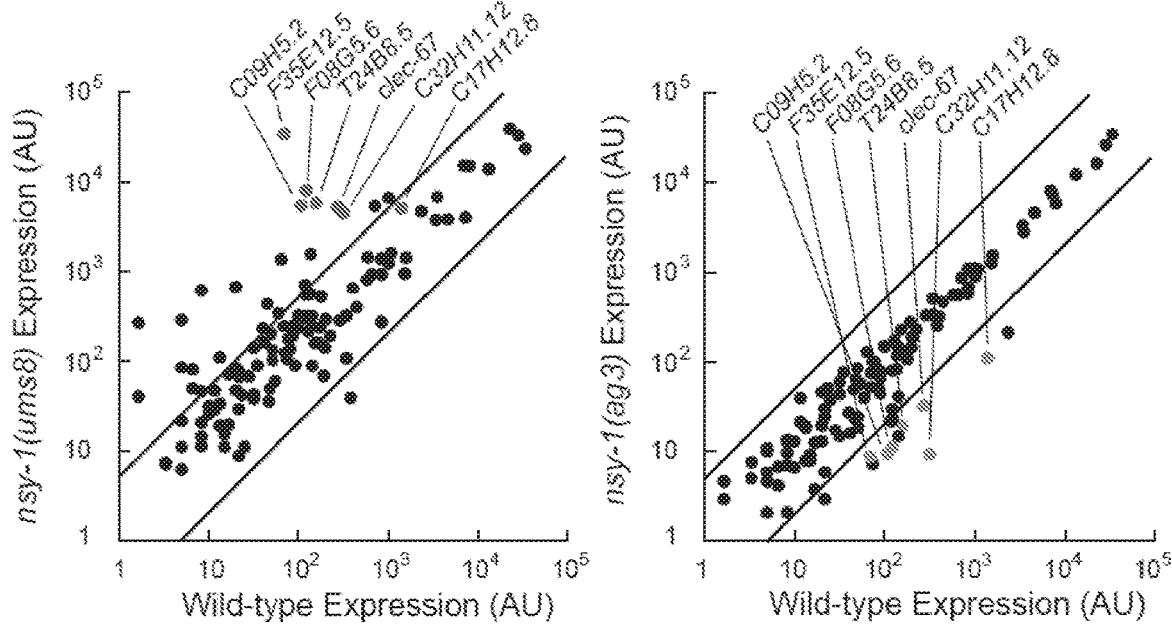
FIG. 13(A): A scatter plot compares the expression of one hundred eighteen (118) *C. elegans* genes, which were analyzed using nanoString nCounter gene expression system in wild-type, nsy-1(ums8) and nsy-1(ag3) nematodes. Data are the average of two replicates for nsy-1(ums8) and nsy-1(ag3), and are from one sample for wild-type. The expression of each gene was normalized to geometric mean of the expression of three control genes. Genes that are outside the two parallel lines on each graph are differentially regulated more than five-fold from the expression in wild-type animals. Genes that are previously characterized targets of the p38 MAPK PMK-1 and were strongly differentially regulated in this experiment are highlighted. See Table 2.

To determine if the basal expression of other genes was hyperactivated in the nsy-1(ums8) allele, a nanoString nCounter system was used to compare the expression profile of the one hundred eighteen (118) innate immune and stress response genes in nsy-1(ums8) gain-of-function, nsy-1(ag3) loss-of-function and wild-type nematodes when the strains were feeding on the normal laboratory food source E. coli OP50. FIG. 13A. Twenty-four (24) of the one hundred eighteen (118) genes in this codeset were transcriptionally upregulated at least five-fold in nsy-1(ums8) mutants compared to wild-type animals. The expression data generated from the nanoString analysis and used in the dot plot presented in FIG. 13A is given. AU equals arbitrary units. Data are sorted by the fold induction in nsy-1(ums8) animals compared to controls. 24 genes were upregulated at least five-fold in the nsy-1(ums8) mutants. 13 genes were downregulated at least five-fold in the nsy-1(ag3) mutant. The 11 genes in the codeset whose basal or pathogen-induced transcription requires p38 MAPK PMK-1 (Troemel et al. 2006; Bolz et al. 2010) and the 13 genes in the codeset that in a previous study required PMK-1 for their induction by R24 (Pukkila-Worley et al. 2014) are also annotated. Table 2.

TABLE 2

Relative Expression of the 118 Genes in the nanoString nCounter Gene Expression Analysis.

| Gene ID | Gene Name | Wild-type Expression (AU) | nsy-1(ums8) Expression (AU) | nsy-1(ag3) Expression (AU) | Fold Change nsy-1(ums8) v. wild-type | Fold Change nsy-1(ag3) v. wild-type | Basal or pathogen-induced expression is PMK-1-dependent | Induction by R24 is PMK-1-dependent |
|---|---|---|---|---|---|---|---|---|
| F35E12.5 | | 69.7 | 34,443.0 | 8.7 | 493.9 | −8.0 | Yes | Yes |
| F49F1.1 | | 1.7 | 268.6 | 4.7 | 161.8 | 2.8 | | Yes |
| K11G9.6 | mtl-1 | 8.3 | 620.8 | 9.6 | 74.8 | 1.2 | | |
| F08G5.6 | | 122.9 | 8,073.9 | 11.3 | 65.7 | −10.9 | Yes | Yes |
| K08C7.5 | fmo-2 | 5.0 | 288.3 | 5.9 | 57.9 | 1.2 | | |
| C09H5.2 | | 107.9 | 5,445.5 | 9.3 | 50.4 | −11.6 | Yes | |
| T24B8.5 | | 157.8 | 5,868.3 | 19.2 | 37.2 | −8.2 | Yes | Yes |
| F49F1.7 | | 19.9 | 675.4 | 19.3 | 33.9 | −1.0 | | Yes |
| K07C6.3 | cyp-35B2 | 1.7 | 40.5 | 3.0 | 24.4 | 1.8 | | |
| F28F8.2 | acs-2 | 64.8 | 1,375.8 | 126.8 | 21.2 | 2.0 | | |
| F56D6.2 | clec-67 | 272.3 | 5,294.9 | 32.3 | 19.4 | −8.4 | Yes | Yes |
| T05A10.5 | scl-22 | 5.0 | 85.5 | 10.8 | 17.2 | 2.2 | | |
| C32H11.12 | | 317.2 | 4,535.8 | 9.3 | 14.3 | −34.0 | Yes | |
| F49F1.6 | | 6.6 | 81.3 | 6.8 | 12.3 | 1.0 | Yes | Yes |
| F4764.3 | gpdh-1 | 137.8 | 1,569.5 | 82.7 | 11.4 | −1.7 | | |
| F54B8.4 | | 44.8 | 440.1 | 48.8 | 9.8 | 1.1 | | Yes |
| C49G7.5 | irg-2 | 13.3 | 110.3 | 19.0 | 8.3 | 1.4 | | |
| T28H10.3 | | 710.7 | 5,420.7 | 866.0 | 7.6 | 1.1 | | |
| F49H6.13 | | 6.6 | 50.3 | 4.2 | 7.6 | −1.6 | | |
| C02A12.4 | lys-7 | 1,013.0 | 6,697.5 | 895.8 | 6.6 | −1.1 | | |
| C31A11.5 | oac-6 | 119.6 | 711.2 | 21.8 | 5.9 | −5.5 | | Yes |
| Y58A7A.5 | | 39.9 | 232.6 | 27.0 | 5.8 | −1.5 | | |
| T19C9.8 | | 59.8 | 344.0 | 39.9 | 5.8 | −1.5 | | |
| F11D11.3 | | 8.3 | 46.5 | 7.0 | 5.6 | −1.2 | | |
| B0024.4 | | 122.9 | 558.0 | 79.7 | 4.5 | −1.5 | | |
| T24E12.5 | | 31.6 | 141.1 | 14.8 | 4.5 | −2.1 | | |
| C25E10.2 | cyp-33B1 | 5.0 | 21.9 | 4.7 | 4.4 | −1.1 | | |
| K10D11.2 | | 16.6 | 71.6 | 3.8 | 4.3 | −4.4 | | |
| F08F8.5 | numr-1 | 19.9 | 84.7 | 45.6 | 4.2 | 2.3 | | |
| T27F6.8 | | 137.8 | 570.0 | 117.9 | 4.1 | −1.2 | | |
| F59B10.4 | | 11.6 | 47.5 | 21.4 | 4.1 | 1.8 | | |
| F22H10.2 | | 49.8 | 202.0 | 84.6 | 4.1 | 1.7 | | |
| K05B2.4 | | 41.5 | 160.9 | 16.0 | 3.9 | −2.6 | | |
| C17H12.8 | | 1,389.9 | 5,115.1 | 109.7 | 3.7 | −12.7 | Yes | |
| C06B3.7 | | 21.6 | 77.3 | 24.2 | 3.6 | 1.1 | | |
| C07G3.2 | irg-1 | 69.7 | 245.7 | 52.0 | 3.5 | −1.3 | | |
| Y46G5A.20 | | 101.3 | 325.7 | 146.4 | 3.2 | 1.4 | | |
| R11A5.3 | | 10.0 | 31.5 | 6.7 | 3.2 | −1.5 | | |
| F35E8.11 | cdr-1 | 21.6 | 67.6 | 5.9 | 3.1 | −3.7 | | |
| ZC443.6 | ugt-16 | 179.3 | 519.1 | 107.4 | 3.0 | −1.7 | | |
| Y38E10A.15 | nspe-7 | 89.7 | 252.7 | 66.6 | 2.8 | −1.3 | | |
| T24C4.4 | | 89.7 | 245.2 | 43.8 | 2.7 | −2.0 | | |
| F55G11.2 | | 122.9 | 322.0 | 23.1 | 1.6 | −5.3 | | Yes |
| H23N18.1 | ugt-13 | 34.9 | 89.9 | 76.2 | 2.6 | 2.2 | | |
| F14F9.3 | | 10.0 | 25.6 | 12.9 | 2.6 | 1.3 | | |
| K10G4.3 | | 51.5 | 131.9 | 24.4 | 2.6 | −2.1 | | |
| Y56A3A.33 | | 13.3 | 33.5 | 18.3 | 2.5 | 1.4 | | |
| C32H11.1 | | 8.3 | 20.7 | 2.1 | 2.5 | −4.0 | Yes | Yes |
| Y46C8A1.4 | clec-71 | 11.6 | 28.9 | 39.5 | 2.5 | 3.4 | | |
| C29F7.2 | | 589.5 | 1,446.3 | 555.9 | 2.5 | −1.1 | | |
| K08D8.5 | | 122.9 | 299.7 | 29.6 | 2.4 | −4.2 | Yes | |
| K12G11.4 | sodh-2 | 28.2 | 68.3 | 17.2 | 2.4 | −1.6 | | |
| R08H2.1 | dhs-23 | 19.9 | 47.4 | 13.0 | 2.4 | −1.5 | | |
| T28C12.4 | | 99.6 | 234.4 | 149.5 | 2.4 | 1.5 | | |
| C14F5.1 | dct-1 | 78.1 | 177.6 | 98.1 | 2.3 | 1.3 | | |
| F01D5.5 | | 381.9 | 863.3 | 250.9 | 2.3 | −1.5 | | |
| R10E8.3 | | 3.3 | 7.4 | 5.0 | 2.2 | 1.5 | | |
| Y22D7AR.9 | | 86.4 | 191.8 | 52.9 | 2.2 | −1.6 | | |
| K07G6.4 | cyp-35B1 | 142.8 | 317.1 | 14.7 | 2.2 | −9.7 | | |
| F55G11.6 | | 5.0 | 11.0 | 10.0 | 2.2 | 2.0 | | Yes |
| H12D21.1 | nspa-1 | 6,894.8 | 15,290.0 | 8,139.9 | 7.2 | 1.2 | | |
| F08H9.4 | | 3.3 | 7.1 | 7.6 | 2.1 | 2.3 | | |
| Y22F5A.5 | lys-2 | 2,339.8 | 4,733.2 | 211.3 | 2.0 | −11.1 | Yes | Yes |
| K09D9.2 | cyp-35A3 | 51.5 | 102.6 | 18.4 | 2.0 | −2.8 | | |
| F28B4.3 | | 3,483.9 | 6,849,8 | 2,819.0 | 7.0 | −1.2 | | |
| F21F8.3 | asp-5 | 7,914.4 | 15,186.1 | 5,844.3 | 1.9 | −1.4 | | |
| C12C8.1 | hsp-70 | 23.3 | 42.0 | 51.1 | 1.8 | 2.2 | | |
| T19D12.3 | | 8.3 | 14.5 | 12.9 | 1.7 | 1.6 | | |
| F21F8.7 | asp-6 | 22,335.0 | 38,717.5 | 16,404.8 | 1.7 | −1.4 | | |
| W02D9.10 | | 71.4 | 123.4 | 74.8 | 1.7 | 1.0 | | |
| H23N18.3 | ugt-8 | 142.8 | 241.4 | 146.7 | 1.7 | 1.0 | | |

TABLE 2-continued

Relative Expression of the 118 Genes in the nanoString nCounter Gene Expression Analysis.

| Gene ID | Gene Name | Wild-type Expression (AU) | nsy-1(ums8) Expression (AU) | nsy-1(ag3) Expression (AU) | Fold Change nsy-1(ums8) v. wild-type | Fold Change nsy-1(ag3) v. wild-type | Basal or pathogen-induced expression is PMK-1-dependent | Induction by R24 is PMK-1-dependent |
|---|---|---|---|---|---|---|---|---|
| C06B3.3 | cyp-35C1 | 81.4 | 137.0 | 87.0 | 1.7 | 1.1 | | |
| C03G6.15 | cyp-35A2 | 832.0 | 1,394.4 | 577.7 | 1.7 | −1.4 | | |
| K09A9.1 | nipi-3 | 129.5 | 213.7 | 171.7 | 1.6 | 1.3 | | |
| F22B5.4 | | 74.7 | 122.1 | 99.6 | 1.6 | 1.3 | | |
| K08F4.7 | gs1-4 | 405.7 | 654.3 | 316.3 | 1.6 | −1.3 | | |
| T10H9.4 | snb-1 | 1,072.7 | 1,626.9 | 1,082.7 | 1.5 | 1.0 | | |
| F42A10.4 | efk-1 | 202.6 | 293.7 | 187.0 | 1.4 | −1.1 | | |
| C32H11.3 | | 13.3 | 19.1 | 8.0 | 1.4 | −1.7 | | |
| R03D7.6 | gst-5 | 654.3 | 934.0 | 558.8 | 1.4 | −1.2 | | |
| F52F10.4 | oac-32 | 74.7 | 105.4 | 7.7 | 1.4 | −10.3 | | |
| ZC376.7 | atfs-1 | 581.2 | 813.6 | 556.3 | 1.4 | −1.0 | | |
| F59A7.1 | clec-206 | 8.3 | 11.3 | 13.4 | 1.4 | 1.6 | | |
| C37C3.10 | | 21.6 | 29.4 | 3.0 | 1.4 | −7.3 | | |
| C08A9.1 | sod-3 | 31.6 | 42.9 | 59.3 | 1.4 | 1.9 | | |
| T21E8.1 | pgp-6 | 176.0 | 238.2 | 128.0 | 1.4 | −1.4 | | |
| ZK1037.5 | nhr-247 | 5.0 | 6.2 | 2.1 | 1.2 | −2.4 | | |
| F45D3.4 | | 1,004.7 | 1,240.2 | 1,112.6 | 1.2 | 1.1 | | |
| F38E11.1 | hsp-12.3 | 31.6 | 38.3 | 43.4 | 1.2 | 1.4 | | |
| Y38A10A.5 | crl-1 | 27,937.8 | 33,250.9 | 26,336.0 | 1.2 | −1.1 | | |
| F38E11.2 | hsp-12.6 | 16.6 | 19.6 | 12.6 | 1.2 | −1.3 | | |
| F43E2.8 | hsp-4 | 3,379.3 | 3,795.2 | 3,315.7 | 1.1 | −1.0 | | |
| F37812.2 | gcs-1 | 841.9 | 938.4 | 679.8 | 1.1 | −1.2 | | |
| ZK697.6 | gst-21 | 54.8 | 59.8 | 56.3 | 1.1 | 1.0 | | |
| C15H9.6 | hsp-3 | 13,135.3 | 14,027.1 | 12,268.3 | 1.1 | −1.1 | | |
| F26A3.4 | | 152.8 | 158.3 | 225.4 | 1.0 | 1.5 | | |
| M176.1 | arrd-3 | 15.0 | 15.4 | 9.2 | 1.0 | −1.6 | | |
| T19H12.1 | ugt-9 | 48.2 | 49.7 | 64.0 | 1.0 | 1.3 | | |
| C32D5.12 | | 288.9 | 282.5 | 330.6 | 1.0 | 1.1 | | |
| C02134.2 | nhr-17 | 93.0 | 89.9 | 77.1 | 1.0 | −1.2 | | |
| F53E10.4 | irg-3 | 169.4 | 159.4 | 123.3 | 0.9 | −1.4 | | |
| F36A4.7 | ama-1 | 345.4 | 323.6 | 331.7 | 0.9 | −1.0 | | |
| C15F1.7 | sod-1 | 1,574.2 | 1,436.6 | 1,547.3 | 0.9 | −1.0 | | |
| C34G6.4 | pgp-2 | 445.0 | 399.7 | 464.2 | 0.9 | 1.0 | | |
| C37H5.8 | hsp-6 | 4,598.2 | 3,869.2 | 4,633.8 | 0.8 | 1.0 | | |
| T22137.3 | | 227.5 | 190.4 | 228.3 | 0.8 | 1.0 | | |
| ZK896.5 | | 46.5 | 35.7 | 23.3 | 0.8 | −2.0 | | |
| Y51B9A.8 | | 15.0 | 11.1 | 8.0 | 0.7 | −1.9 | | |
| C49C8.4 | cyo-33E1 | 197.6 | 141.3 | 143.4 | 0.7 | −1.4 | | |
| T04C12.6 | act-1 | 33,346.4 | 23,492.5 | 34,531.8 | 0.7 | 1.0 | | |
| F35G2.4 | phy-2 | 1,531.1 | 958.5 | 1,268.7 | 0.6 | −1.2 | | |
| Y38E10A.5 | clec-4 | 142.8 | 89.2 | 40.8 | 0.6 | −3.5 | | |
| Y22D7AL.5 | hsp-60 | 7,221.9 | 4,052.9 | 7,331.1 | 0.6 | 1.0 | | |
| Y46H3A.3 | hsp-16.2 | 24.9 | 11.1 | 37.7 | 0.4 | 1.5 | | |
| Y46H3A.2 | hsp-16.41 | 21.6 | 8.8 | 30.0 | 0.4 | 1.4 | | |
| T27E4.3 | hsp-16.48 | 192.6 | 68.8 | 274.4 | 0.4 | 1.4 | | |
| F44E5.5 | | 838.6 | 272.8 | 1,097.6 | 0.3 | 1.3 | | |
| T27E4.8 | hsp-16.1 | 345.4 | 108.2 | 506.9 | 0.3 | 1.5 | | |

Seven (7) of the twenty-four (24) genes most strongly upregulated in the nsy-1(ums8) gain-of-function allele were among the twelve (12) most strongly reduced in the nsy-1 (ag3) loss-of-function allele (F08G5.6, F35E12.5, C09H5.2, T24B8.5, clec-67, C32H11.12, and oac-6). FIG. 13A and Table 2.

This group of seven (7) genes includes F08G5.6 and five other putative immune effectors (F35E12.5, C09H5.2, T24B8.5, C32H11.12 and clec-67) that are previously characterized targets of the p38 MAPK PMK-1. Table 2; and Troemel et al., "p38 MAPK regulates expression of immune response genes and contributes to longevity in C. elegans" PLoS Genet. 2:e183 (2006). Of note, the codeset included four additional genes whose basal or pathogen-induced expression requires the p38 MAPK PMK-1 (F49F1.6, C17H12.8, C32H11.1, K08D8.5, lys-2) and each of these genes was induced at least two-fold in the nsy-1(ums8) mutants and repressed at least four-fold in the nsy-1(ag3) mutants. Table 2.

In addition, this codeset was previously used to identify thirteen (13) genes whose induction by the immunostimulatory anti-infective xenobiotic R24 was dependent on the p38 MAPK PMK-1. Pukkila-Worley et al., "The evolutionarily conserved mediator subunit MDT-15/MED15 links protective innate immune responses and xenobiotic detoxification" PLoS Pathog. 10:e1004143 (2014). Nine (9) of these thirteen (13) genes were upregulated more than five-fold and all of these genes were induced at least two-fold in the nsy-1(ums8) gain-of-function mutant. Table 2. Thus, the nsy-1(ums8) gain-of-function allele drives the constitutive activation of genes whose basal, pathogen-induced or R24-induced expression is dependent the p38 MAPK pathway.

Figure 13B:
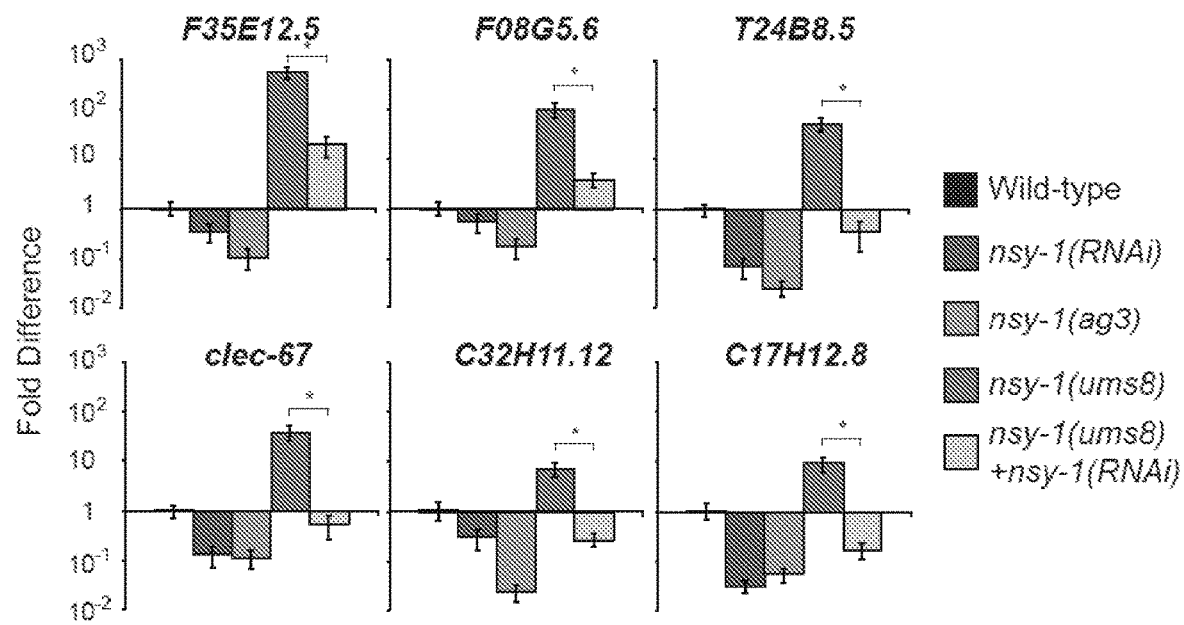
FIG. 13(B); qRT-PCR was used to study the expression of six putative immune effectors in RNAi-treated, mixed stage nematodes of the indicated genotypes. All nematodes were grown on the RNAi bacteria feeder strain HT115 expressing the empty vector L4440, except for the two indicated samples that were exposed to bacteria expressing the nsy-1 (RNAi) construct. The location on the scatter plots of these genes is indicated in FIG. 12(A) with (left) and right dots. Data are the average of three replicates each normalized to a control gene with error bars representing SEM, and are presented as the value relative to the average expression of the indicated gene in wild-type animals. * equals p<0.05.

These data were confirmed in three biological replicate samples using qRT-PCR evaluation of six (6) putative immune effectors that were differentially regulated in the nanoString analysis and are known targets of the p38 MAPK pathway. All six genes were transcriptionally repressed in nsy-1(RNAi) and nsy-1(ag3) loss-of-function mutants, and were upregulated in the nsy-1(ums8) allele RNAi-mediated knockdown of nsy-1 partially suppressed the constitutive activation of these six putative immune effectors in the nsy-1(ums8) allele. FIG. 13B.

Figure 10A:
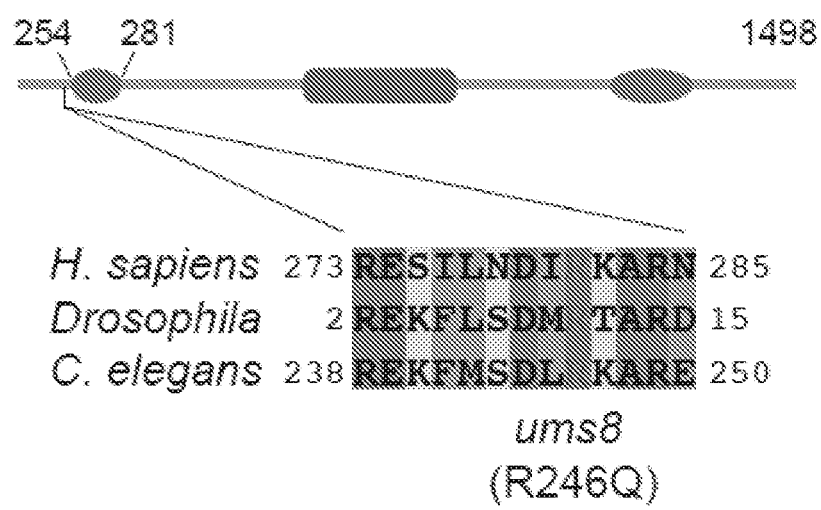
FIG. 10(A): A putative domain architecture schematic of NSY-1, based on homology to mammalian ASK1 is presented. Bunkoczi et al., "Structural and functional characterization of the human protein kinase ASK1" Structure 15:1215-1226 (2007). The putative location of the central serine-threonine kinase domain and two coiled-coil domains in the N and C termini are shown. The boundary of the N-terminal negative regulatory domain relative to the NSY-1 protein is presented above the diagram. The Arg that was mutated to Gln in the ums8 strain (R246Q) is shown. Amino acid sequence alignment of human ASK1, *Drosophila* Pk92B (the ASK1 homolog) and *C. elegans* NSY-1 demonstrates that the ums8 mutation is located in a strongly conserved region. Dark shading indicates identical amino acids with progressive lighter shading indicating the level of similarity in amino acid class as determined by the software ClustalW2.
Figure 10B:
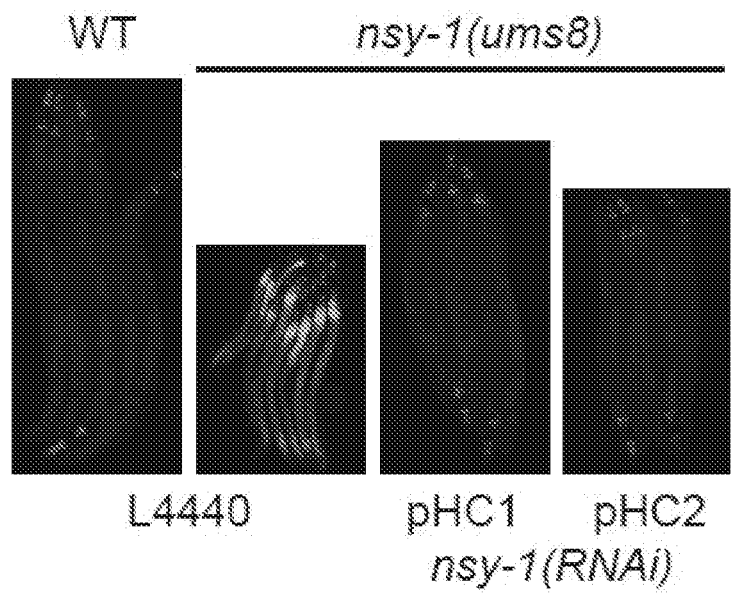
FIG. 10(B): Wild-type (WT) and nsy-1(ums8) animals were exposed to the feeding RNAi bacteria strain transformed with the control vector (L4440) or with two separate RNAi constructs (pHC1 and pHC2) that target different areas of coding region in the nsy-1 gene and photographed. Green is F08G5.6::GFP induction and red is myo-2::mCherry, which was used as the co-injection marker.
Figure 10C:
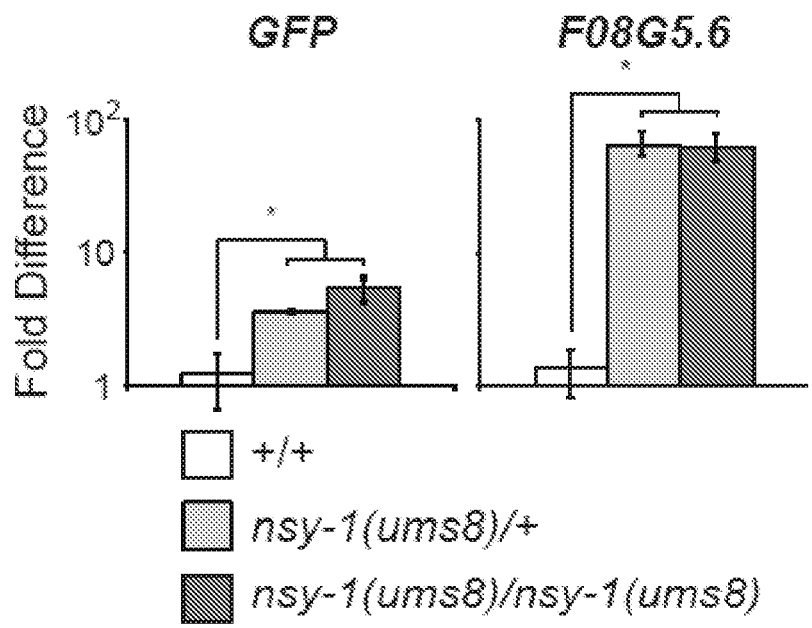
FIG. 10(C): The expression of the indicated genes was determined using qRT-PCR in wild-type (+/+), nsy-1 (ums8)/+heterozygotes and nsy-1(ums8)/nsy-1(ums8) homozygotes. F08G5.6::GFP was used as the wild-type strain. Data are the average of three replicates each normalized to a control gene with error bars representing SEM, and are presented as the value relative to the average expression of the indicated gene in wild-type animals. * equals $p<0.05$. There was no statistical difference in the levels of induction between the heterozygous and homozygous samples for either gene.
Figure 11A:
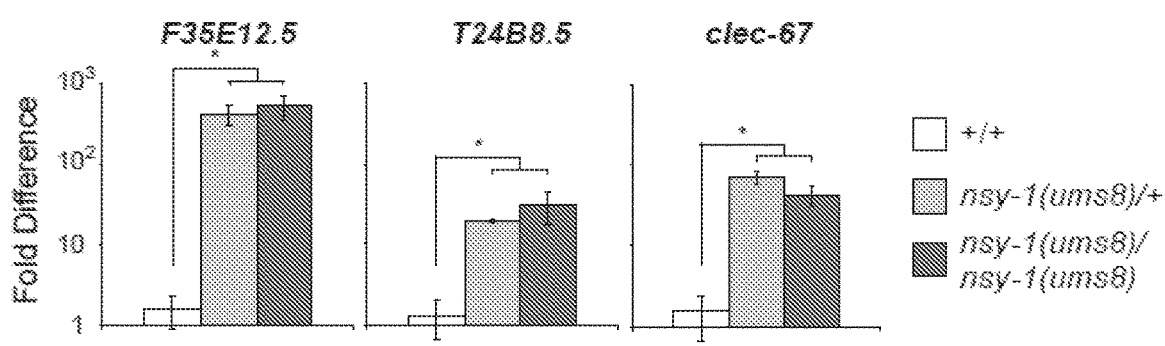
FIG. 11A: The expression of the indicated genes was determined using qRT-PCR in wild-type (+/+), nsy-1 (ums8)/+heterozygotes and nsy-1(ums8)/nsy-1(ums8) homozygotes. Data are the average of three replicates each normalized to a control gene with error bars representing SEM, and are presented as the value relative to the average expression of the indicated gene in wild-type animals. * equals $p<0.05$. There was no statistical difference in the levels of induction between the heterozygous and homozygous samples.
Figure 11B:
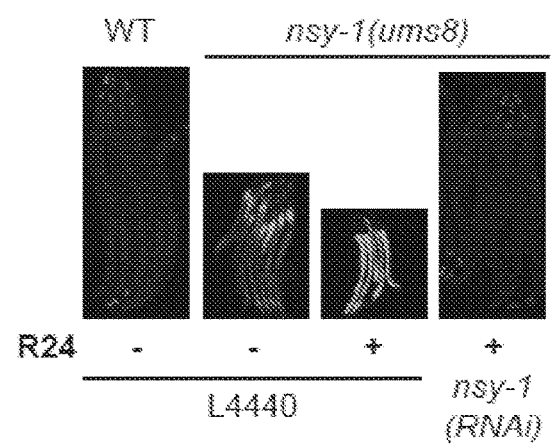
FIG. 11B: Wild-type (WT) and nsy-1(ums8) animals were exposed to the feeding RNAi bacteria strain transformed with the control vector (L4440) or with an RNAi constructs (pHC1) that targets nsy-1 gene. Animals at the L4 stage were transferred to plates containing 70 μM R24 (+) or the solvent control (−), as indicated. Green is F08G5.6::GFP induction and red is myo-2::mCherry, which was used as the co-injection marker.

In addition, nsy-1(ums8)/+heterozygotes found to cause the induction of three p38 MAPK-dependent immune effectors had levels equivalent to that in nsy-1(ums8) homozygous nematodes, as observed for F08G5.6. FIG. 11A and FIG. 10C. Of note, the nsy-1(ums8) mutant was exposed to R24 where F08G5.6::GFP expression was markedly increased as compared to untreated nsy-1(ums8) animals. These data suggest that the effects of R24 and the nsy-1 gain-of-function allele on gene expression are additive. FIG. 11B. Consistent with this observation, R24 was previously found to enhance the expression of *P. aeruginosa* immune effectors that are induced during bacterial infection. (infra).

Previous whole genome, transcriptome profiling analyses have identified a group of putative immune effectors whose basal expression is strongly repressed in pmk-1(km25) mutants. Troemel et al., "p38 MAPK regulates expression of immune response genes and contributes to longevity in *C. elegans*" *PLoS Genet.* 2:e183 (2006). The term basal regulation has been used in this context to describe the expression of genes in animals that are growing on the laboratory food source (*E. coli* OP50) and is used to distinguish from the pathogen-induced expression of putative immune effectors that is observed during microbial infection. In addition to controlling the basal expression of putative immune effectors, a number of studies have demonstrated that the p38 MAPK PMK-1 is also required for the pathogen-induced expression of putative immune effectors. Troemel et al., "p38 MAPK regulates expression of immune response genes and contributes to longevity in *C. elegans*" *PLoS Genet.* 2:e183 (2006); Bolz et al., "A conserved PMK-1/p38 MAPK is required in *Caenorhabditis elegans* tissue-specific immune response to *Yersinia pestis* infection" *J Biol Chem* 285:10832-10840 (2010); and Pukkila-Worley et al., "Stimulation of host immune defenses by a small molecule protects *C. elegans* from bacterial infection" *PLoS Genet.* 8:e1002733 (2012).

It also is clear, however, that there is a group of genes, the identities of which have not been comprehensively defined, that require the p38 MAPK PMK-1 pathway for their induction, but not for their basal expression. The nanoString data of nsy-1(ums8) mutant indicates that this gain-of-function allele can be used to identify this group of innate immune effectors. Of the twenty-four (24) genes in the codeset that were most strongly induced in the nsy-1(ums8) mutant, seventeen (17) were not dependent on NSY-1 for their basal expression, a group which includes both pathogen and stress-response genes. Table 2.

It is also interesting to note that genes involved in the detoxification of small molecule toxins, such as cytochrome P450s (CYPs), glutathione-s-transferases (GSTs), and UDP-glucuronosyltransferases (UDPs), were not among those transcriptionally upregulated in the nsy-1(ums8) gain-of-function allele. Table 2. It has been previously observed that the anti-infective xenobiotic R24 caused a robust induction of these gene classes, in addition to genes involved in the response to pathogens. Unlike the induction of antimicrobial immune effectors, however, the upregulation of detoxification genes by R24 was not dependent on the p38 MAPK PMK-1 pathway. Pukkila-Worley et al., "Stimulation of host immune defenses by a small molecule protects *C. elegans* from bacterial infection" *PLoS Genet.* 8: e1002733 (2012); and Pukkila-Worley et al., The evolutionarily conserved mediator subunit MDT-15/MED15 links protective innate immune responses and xenobiotic detoxification. *PLoS Pathog.* 10:e1004143 (2014).

Figure 6:
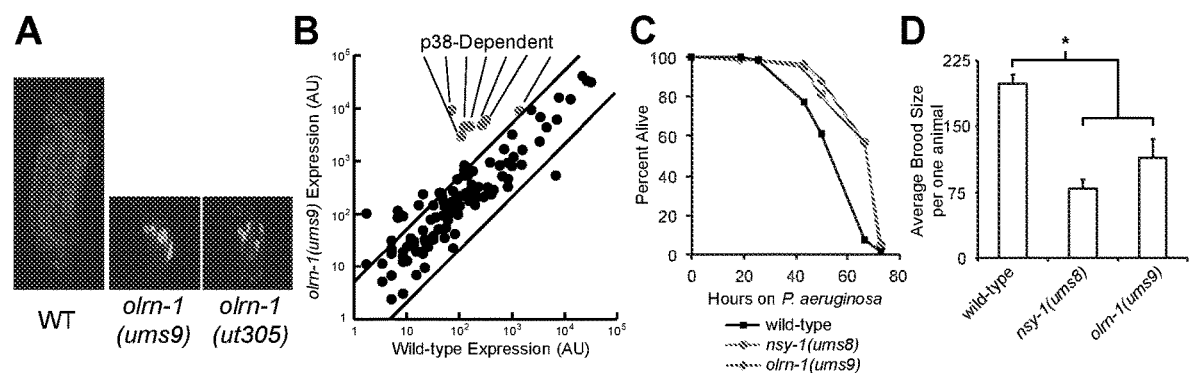
FIG. 6 presents exemplary data showing that a mutated ORLN-1 receptor results in a hyperactive nematode immune response.

Accordingly, nsy-1(ums8) nematodes are resistant to infection with *P. aeruginosa*. FIG. 6C. Further, nsy-1(ums8) nematodes have a markedly smaller brood size and are delayed in development compared to wild-type nematodes. FIG. 6D and FIG. 5A, respectively. These data are consistent with the immunostimulatory xenobiotic R24 effects discussed above. Thus, aberrant stimulation of p38 MAPK PMK-1-mediated innate immune responses via a gain-of-function mutation in nsy-1 or treatment with the anti-infective R24 may drive an immune response that is protective to nematodes during a bacterial infection, but are toxic (e.g., autoimmune) to nematodes under normal growth conditions.

The human homolog of NSY-1, ASK1, regulates p38 activity through at least three conserved protein domains: a central serine-threonine kinase domain and two coiled-coil domains in the N and C termini. FIG. 5D and Bunkoczi et al., (2007). The ASK1 N-terminal domain binds thioredoxin (TRX), which inhibits the function of NSY-1. Furthermore, the nematode gain-of-function ums8 mutation is located in a strongly conserved region, eight amino acids upstream of the NSY-1 region predicted by homology to encode the ASK1 N-terminal regulatory domain. Thus, the activity of the MAPKKK NSY-1 may be tightly controlled by a negative regulatory element, which is believed to function as part of a physiological mechanism to control p38 MAPK-mediated innate immune hyperactivation and ensure cellular homeostasis in nematodes (e.g., for example, *C. elegans*).

To explore further the physiological consequences of innate immune hyperactivation in *C. elegans*, a forward genetic screen was designed to identify endogenous activators of p38 MAP kinase PMK-1 signaling. The innate immune transcriptional reporter F08G5.6::GFP is induced during *P. aeruginosa* infection, and robustly by the anti-infective xenobiotic R24, in a manner dependent on the p38 MAPK PMK-1 pathway. Pukkila-Worley et al., "Stimulation of host immune defenses by a small molecule protects *C. elegans* from bacterial infection" *PLoS Genet.* 8:e1002733 (2012); and Pukkila-Worley et al., "The evolutionarily conserved mediator subunit MDT-15/MED15 links protective innate immune responses and xenobiotic detoxification" *PLoS Pathog.* 10:e1004143 (2014). A screen to identify dominant activators of F08G5.6::GFP that cause constitutive activation of the p38 MAPK pathway was developed. For example, the F1 progeny of mutagenized F08G5.6::GFP nematodes were screened, a single mutant allele, ums8, was identified from approximately one hundred seventy thousand (170,000) mutagenized haploid genomes.

Following both 1× and 2× outcrosses to wild-type N2 animals, F2 recombinants that were homozygous for the mutant phenotype were pooled and these genomes were sequenced using next-generation sequencing technology. These data revealed that the ums8 mutant contained a G→A missense mutation in the coding region of nsy-1 that resulted in the substitution of a strongly conserved Arg246 to Gln246. FIG. 10A. NSY-1/ASK1 is a conserved MAPKKK that acts upstream of the p38 MAPK PMK-1 to regulate immune and stress responses in *C. elegans*. Kim et al., "A conserved p38 MAP kinase pathway in *Caenorhabditis elegans* innate immunity" *Science* 297:623-626 (2002). The ums8 strain was outcrossed a total of six times to wild-type N2 and confirmed that the R246Q mutation was present and F08G5.6::GFP expression was activated in the outcrossed strain.

Figure 12A:
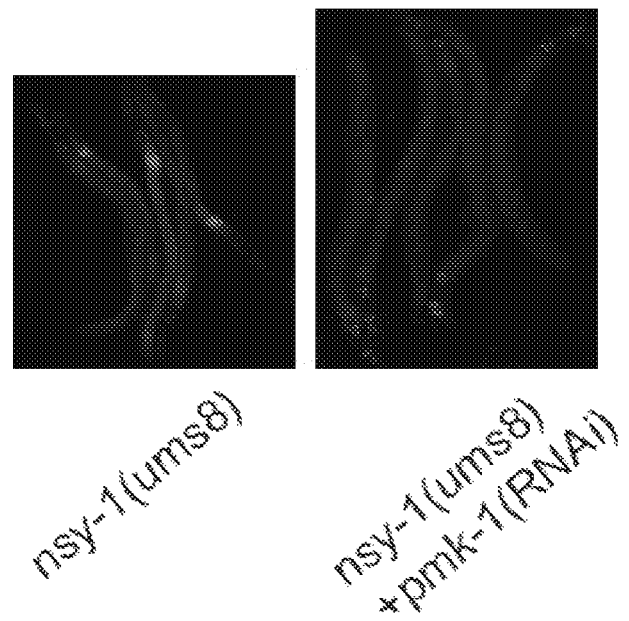
FIG. 12(A): nsy-1(ums8) animals were exposed to the feeding RNAi bacteria strain transformed with the control vector (L4440) or with an RNAi construct that targets the pmk-1 gene and photographed. Green is F08G5.6::GFP induction and red is myo-2::mCherry, which was used as the co-injection marker.

To determine if the constitutive expression of the immune reporter F08G5.6::GFP in the ums8 mutant is caused by the G→A mutation in the coding region of nsy-1, RNAi was used to knockdown the expression of nsy-1 in the ums8 mutant and found that this treatment suppressed F08G5.6:: GFP induction. FIG. 10B. Moreover, RNAi-mediated knockdown of nsy-1 in wild-type animals did not cause F08G5.6 induction. In addition, F08G5.6::GFP induction in the nsy-1(ums8) strain was suppressed by RNAi-mediated knockdown of pmk-1, the p38 MAPK that is downstream of nsy-1. FIG. 12A. qRT-PCR then confirmed that nsy-1(ums8) is a dominant, gain-of-function allele that drives both the constitutive activation of the F08G5.6::GFP and the F08G5.6 gene itself. FIG. 10C. F08G5.6 and GFP were induced to a similar degree in nsy-1(ums8)/+heterozygotes and in nsy-1(ums8)/nsy-1(ums8) homozygotes compared to wild-type controls that carried the transgene F08G5.6::GFP (+/+).

Figure 10D:
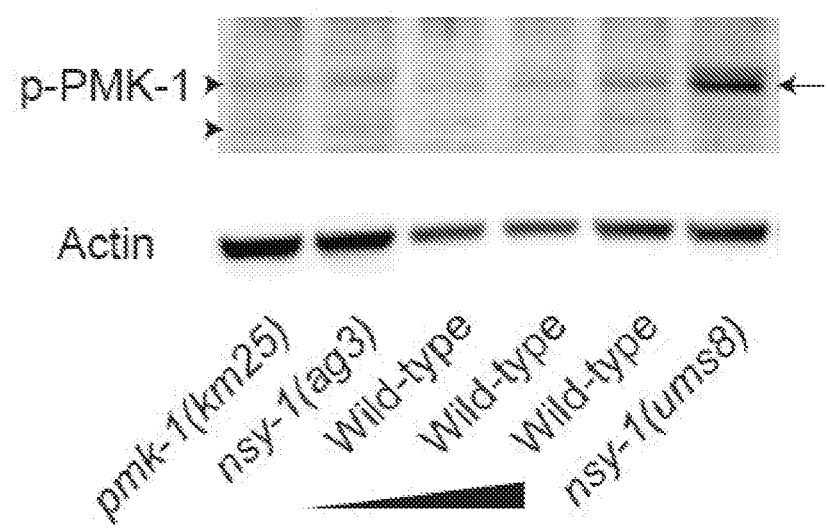
FIG. 10(D): Immunoblot analysis of lysates from L4 larval stage animals of the indicated genotype using antibodies that recognize the doubly phosphorylated TGY motif of PMK-1 (p-PMK-1) and actin. Thirty μg of nsy-1(ums8), pmk-1(km25) and nsy-1(ag3) total protein were loaded on the gel alongside a dilution series of wild-type template [15 μg, 20 μg and 30 μg of total protein (left to right)] to control for the ability of the p-PMK-1 antibody to detect different concentrations of substrate. The arrow on the right highlights the PMK-1 band, which is absent in the pmk-1(km25) and nsy-1(ag3) mutants. The arrowheads on the left point to non-specific bands. Data are representative of two biological replicates.

To confirm that nsy-1(ums8) is a gain-of-function allele of nsy-1, an immunoblot analysis of protein lysates from nsy-1(ums8) nematodes was performed where it was found that the nsy-1(ums8) nematodes had greater amounts of activated p38 MAPK PMK-1 than control animals. FIG. 10D.

In summary, these data characterize a gain-of-function allele of the MAPKKK nsy-1 that causes hyperactivation of the p38 MAPK pathway. These data suggest that p38 MAPK innate immune hyperstimulation itself does not lead to the induction small molecule detoxification responses, and that other cellular mechanisms are engaged to recognize and respond to xenobiotic toxins in *C. elegans*.

2. G Protein-Coupled Receptor OLRN-1 Mutations

Pharmaceutical compounds often induce loss-of-function of their target. For example, two (2) of the four (4) mutants identified herein in forward *C. elegans* genetic screens demonstrated a constitutive activation of innate immune responses and each contained nonsense mutations in the G protein-coupled receptor OLRN-1 (e.g., olrn-1(ums9) and olrn-1(ums11)). FIG. 6A. These two mutations were confirmed to contain an early stop codon in the mRNA sequence of olrn-1, resulting in a protein loss-of-function. It was further found that RNAi-mediated knockdown of olrn-1 in the F08G5.6::GFP reporter strain caused constitutive expression of F08G5.6::GFP. In addition, a previously characterized loss-of-function allele, olrn-1(ut305), also caused constitutive F08G5.6::GFP activation. FIG. 6A.

Several observations indicate that the OLRN-1 receptor may be a negative regulator of p38 MAPK-dependent innate immune responses in *C. elegans*. For example, a nanoString experiment provided data showing that several p38 MAPK-dependent genes were markedly elevated in the olrn-1 loss-of-function mutants as compared to controls. FIG. 6B. Accordingly, the olrn-1(ums9) mutants were more resistant to killing by *P. aeruginosa*. FIG. 6C. Further, the olrn-1 (ums9) mutant is toxic to nematodes in a manner similar to the above observations with the immunostimulatory molecule R24 and with the gain-of-function allele nsy-1(ums8). olrn-1(ums9) mutants are markedly delayed developmentally and have a smaller brood size compared to controls. FIG. 6A and FIG. 6D, respectively.

Thus, a gain-of-function mutation in nsy-1 and a loss-of-function in olrn-1 phenocopy the administration of the R24: animals are protected from bacterial infection, but hyperactivation of p38 MAPK responses is toxic to nematodes. In particular, loss-of-function mutations in olrn-1 cause immune hyperactivation, which is toxic to nematodes. OLRN-1 has one-to-one orthologs in all of the most medically relevant pathogenic nematodes, but is not present in mammals. Thus, the data presented herein suggest that the GPCR OLRN-1 is a druggable target, antagonism of which can selectively drive an (auto)immune hyperactivation and kill a broad range of parasitic nematodes without affecting human immune function.

Figure 8:
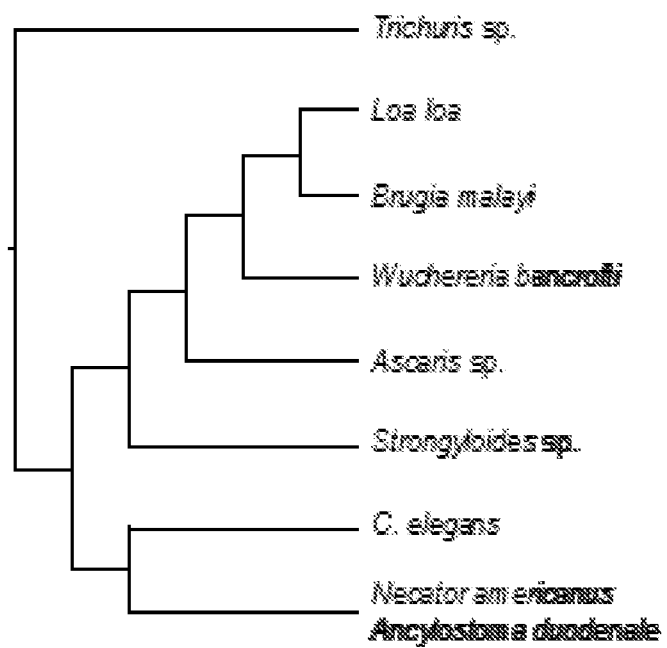
FIG. 8 presents a proposed phylogenetic tree of OLRN-1 homologs in pathogenic nematodes. Homolog in *Onchocerca* sp. is not shown.

The OLRN-1 receptor is believed to be conserved in nearly all of clinically relevant pathogenic nematodes, but it is not present in mammals (e.g., humans). FIG. 8. Thus, a low molecular weight inhibitor of OLRN-1 should be selectively toxic to pathogenic nematodes, and not adversely affect humans. Moreover, GPCRs are among the most common drug targets in all of pharmacology and comprise more than half of all the commercially available medications on the market.

D. Endogenous Immune Hyperactivation Protects Against Nematode Bacterial Infection but is Lethal to Uninfected Nematodes Stimulation of the p38 MAPK pathway by the small molecule xenobiotic R24 is known to protect *C. elegans* from bacterial infection by stimulating immune effector expression through the p38 MAPK pathway. Pukkila-Worley et al., "The evolutionarily conserved mediator subunit MDT-15/MED15 links protective innate immune responses and xenobiotic detoxification" *PLoS Pathog.* 10:e1004143 (2014). Immune hyperactivation in this context has negative physiological consequences to nematodes developing under normal laboratory conditions. In one embodiment, the present invention contemplates a method comprising administering R24 to a nematode comprising a MAPKKK NSY-1 gain-of-function mutation and not infected with a bacteria, such that the nematode undergoes an immune hyperactivation that is toxic to the nematode.

Figure 12B:
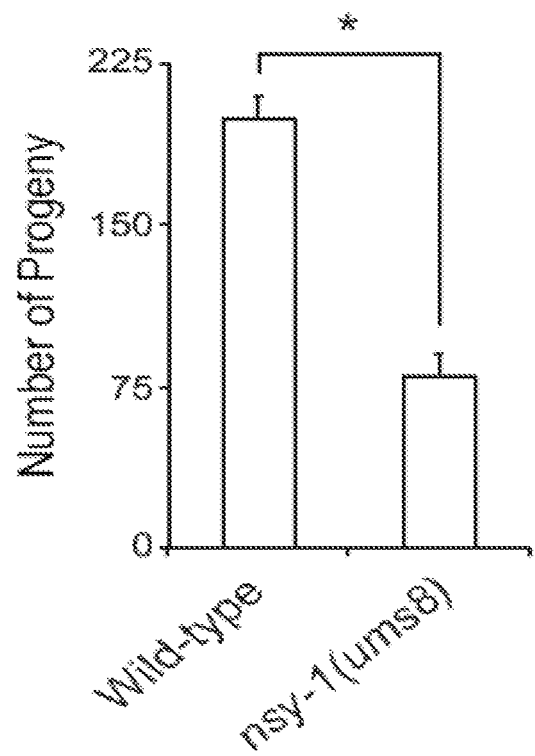
FIG. 12(B): The brood sizes of wild-type and nsy-1 (ums8) animals grown on *E. coli* OP50 were compared. Data are the average brood size from five animals of the indicated genotype with error bars reporting the standard deviation between samples. *$p<0.001$
Figure 12C:
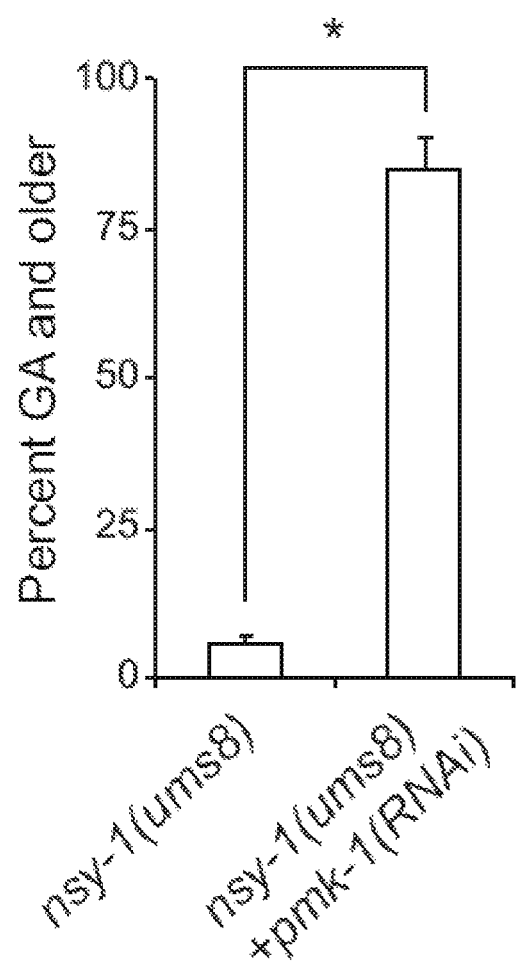
FIG. 12(C): The development of RNAi-treated animals of the indicated genotypes in the presence of 140 μM R24 to the gravid adult stage was recorded. The data are the average of three plates with error bars showing the standard deviation between plates. The sample sizes for this experiment are: nsy-1(ums8)+L4440 (460) and nsy-1(ums8)+pmk-1(RNAi) (386). Data are representative of two biological replicates. *$p<0.001$
Figure 14A:
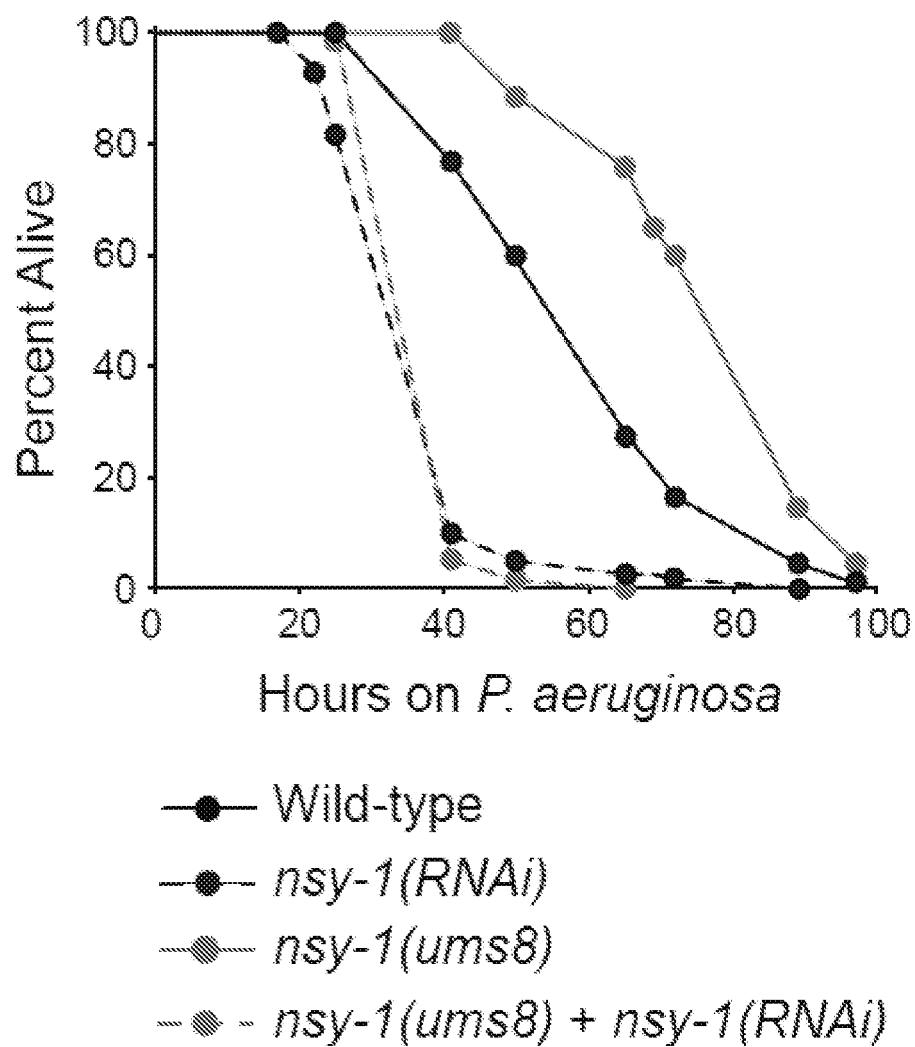
FIG. 14(A): P. aeruginosa pathogenesis assays were performed on RNAi-treated animals of the indicated genotypes. The difference in P. aeruginosa susceptibility between wild-type and nsy-1(ums8) animals is significant, as is the survival difference between nsy-1(ums8) and nsy-1(ums8)+nsy-1(RNAi) (p<0.001). Data are representative of two biological replicates. The sample sizes for this experiment are: wild-type (115), nsy-1(RNAi) (122), nsy-1(ums8) (111) and nsy-1(ums8)+nsy-1(RNAi)(133).
Figure 14B:
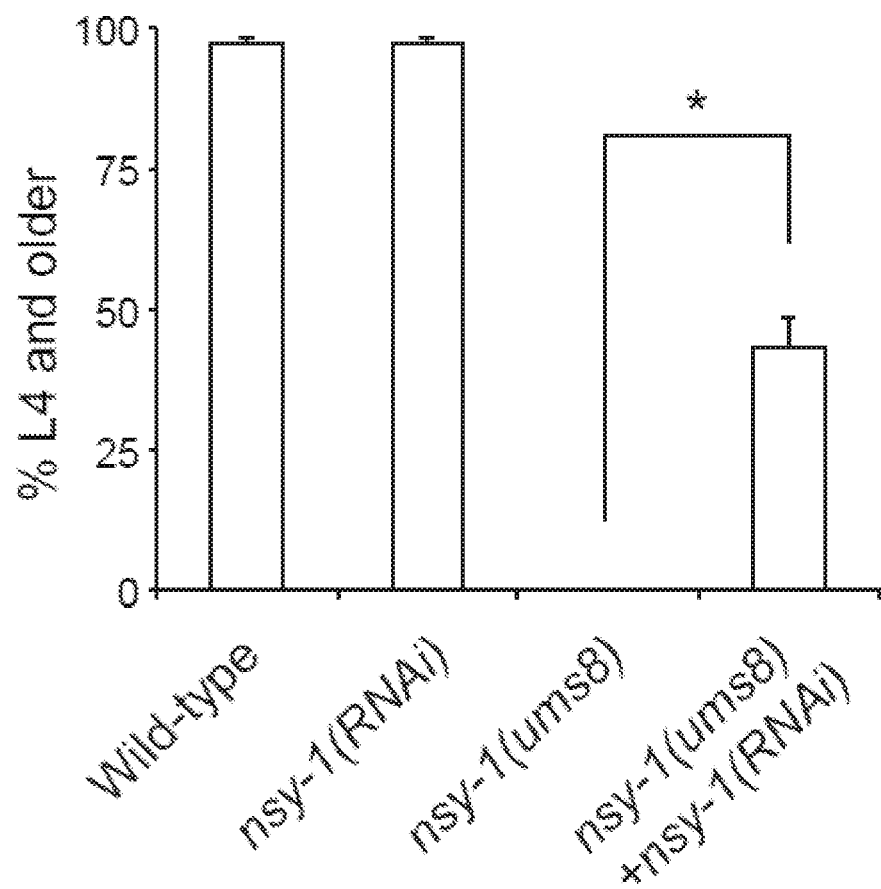
FIG. 14(B): The development of RNAi-treated animals of the indicated genotypes to the L4 larval stage or older was recorded. The data are the average of three plates with error bars showing the standard deviation between plates. The sample sizes for this experiment are: wild-type+L4440 (1,200), wild-type+nsy-1(RNAi) (1,179), nsy-1(ums8)+L4440 (956) and nsy-1(ums8)+nsy-1(RNAi) (1,010). Data are representative of two biological replicates. *p<0.001
Figure 15:
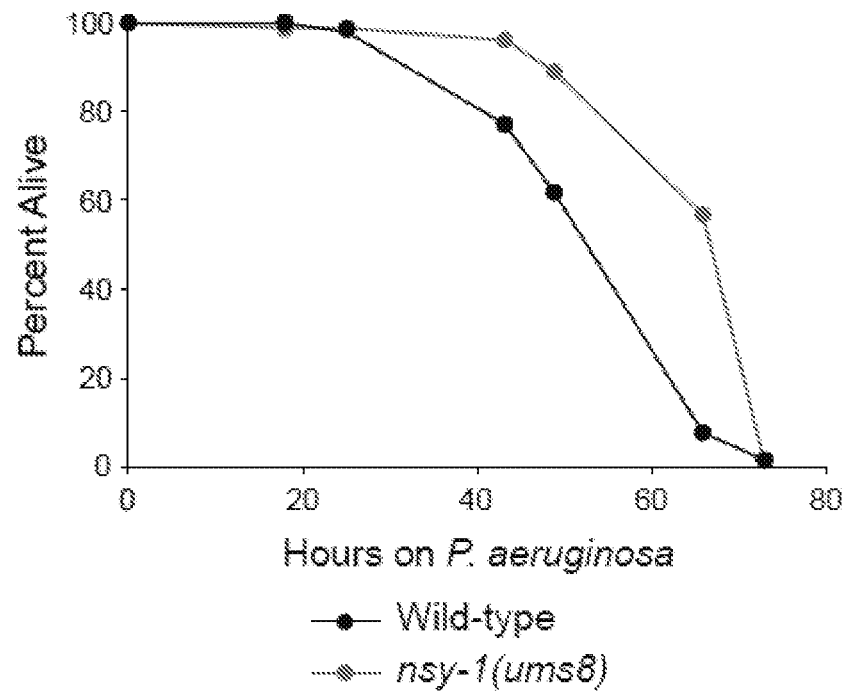
FIG. 15 presents exemplary data showing that nsy-1(ums8) gain-of-function animals are resistant to killing by P. aeruginosa. A P. aeruginosa pathogenesis assay was conducted with C. elegans wild-type and nsy-1(ums8) animals. The difference in susceptibility to P. aeruginosa infection between these two genotypes is significant (p<0.001). Data are representative of two biological replicates. Sample sizes are wild-type (89) and nsy-1(ums8) (84).

Susceptibility of nsy-1(ums8) gain-of-function mutant nematodes to *P. aeruginosa* infection was compared to wild-type nematodes and it was found that nsy-1(ums8) nematodes were resistant to killing by *P. aeruginosa*. FIG. 14A and FIG. 15. Further, RNAi-mediated knockdown of nsy-1 suppressed the resistance phenotype of nsy-1(ums8) nematodes. FIG. 14A. The development of nsy-1(ums8) nematode larvae was markedly delayed compared to wild-type controls, which was quantified by determining the number of mutant and wild-type nematodes that reached the L4 stage from synchronized eggs after three days of incubation at 20° C. FIG. 14B. Knockdown of nsy-1 in nsy-1 (ums8) nematodes partially suppressed this phenotype. FIG. 10B and FIG. 14B. It was also observed that nsy-1(ums8) nematodes had markedly smaller brood sizes than wild-type controls. FIG. 12B. In addition, RNAi-mediated knockdown of pmk-1 also suppressed the delayed development of nsy-1(ums8) nematodes. FIG. 12C.

The data presented herein provides direct evidence from two forward genetic screens that aberrant stimulation of p38 MAPK PMK-1-mediated innate immune responses via a gain-of-function mutation in nsy-1 or the exogenous addition of the anti-infective R24 drives immune responses that are protective during infection, but are toxic to nematodes under normal growth conditions. The alleles with the most penetrant Xts phenotypes all had hypomorphic mutations in the known components of the p38 MAPK pathway. One forward genetic screen for p38 MAPK pathway components also did not identify mutations in any gene that functions upstream of tir-1. Together, these data suggest that the p38

MAPK signaling cassette receives multiple inputs to regulate protective host responses in *C. elegans*.

In addition to promoting clearance of invading pathogens, an emerging body of literature has established that host systems also function to promote tolerance to infection, thereby reducing the negative impact that infection can have on organismal fitness. Ayres et al., "A Signaling Protease Required for Melanization in *Drosophila* Affects Resistance and Tolerance of Infections" *Plos Biol* 6:e305 (2008); and Ayres et al., "The role of anorexia in resistance and tolerance to infections in *Drosophila*" *Plos Biol* 7:e1000150 (2009). Conceptually, host tolerance mechanisms function to mitigate the damage caused by the pathogen and also limit collateral damage associated with immune activation. Ayres et al., "Tolerance of infections" *Annu. Rev. Immunol.* 30:271-294 (2012); and Medzhitov et al., "Disease Tolerance as a Defense Strategy" *Science* 335:936-941 (2012).

The immunostimulatory xenobiotic R24 and the nsy-1 (ums8) gain-of-function allele data discussed herein suggest that such host tolerance mechanisms may function in nematodes to limit the immunopathology associated with aberrant p38 MAPK activation and the ensuing hyperproduction of immune effectors. For example, in *C. elegans*, the endoplasmic reticulum unfolded protein response (UPR) is one such mechanism that has been shown to promote tolerance during immune activation. Richardson et al., "An essential role for XBP-1 in host protection against immune activation in *C. elegans*" *Nature* 463:1092-1095 (2010); and Sun et al., "Neuronal GPCR controls innate immunity by regulating noncanonical unfolded protein response genes" *Science* 332: 729-732 (2011). The IRE1-XBP1/Hacl branch of the UPR is believed to handle the physiological stress associated with an increase in p38 MAPK PMK-1 activity, which was conferred experimentally by exposure to *P. aeruginosa* or through RNAi-mediated knockdown of the MAPK phosphatase vhp-1, a negative regulator of PMK-1. Mizuno et al., "The *Caenorhabditis elegans* MAPK phosphatase VHP-1 mediates a novel JNK-like signaling pathway in stress response" *EMBO J* 23:2226-2234 (2004); and Kim et al., "Integration of *Caenorhabditis elegans* MAPK pathways mediating immunity and stress resistance by MEK-1 MAPK kinase and VHP-1 MAPK phosphatase" *Proc Natl Acad Sci USA* 101:10990-10994 (2004).

Figure 16:
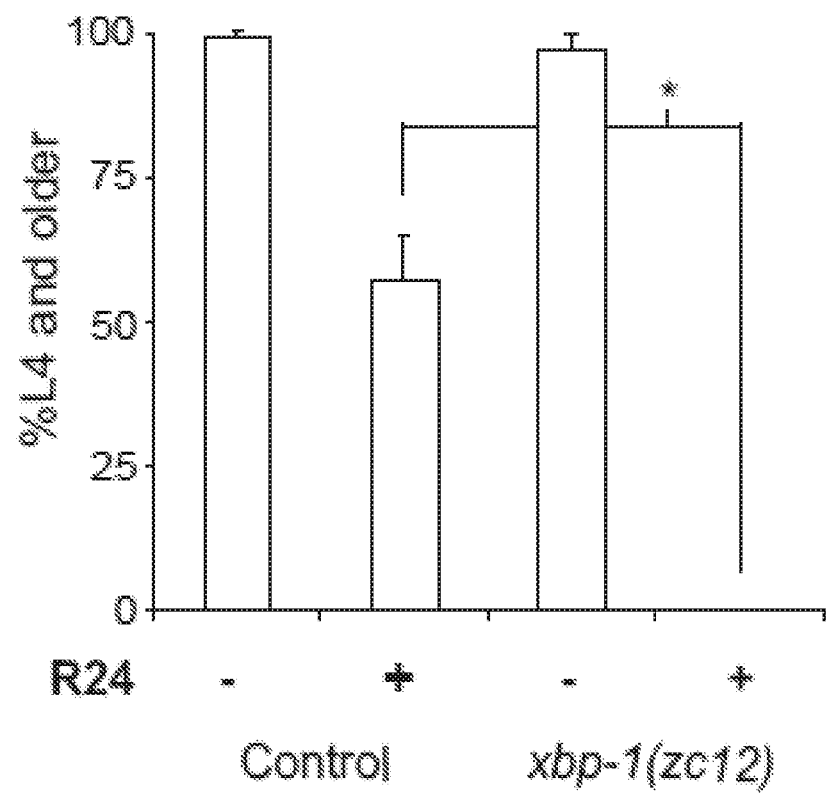
FIG. 16 presents exemplary data that shows the involvement of XBP-1 for nematode development in the presence of the immunostimulatory xenobiotic R24. The percentage of control and xbp-1(zc12) nematodes that grew from eggs to the L4 larval stage in the presence (+) or absence (−) of 70 μM R24 was quantified. Data are presented as the average of three technical replicates with error bars giving the standard deviation between plates and are representative of two biological replicates. For this experiment, zcIs4 was used as the control, as this transgene is also in the background of the xbp-1(zc12) mutant. The sample sizes for this experiment are: Control–173, Control+134, xbp-1(zc12)–152 and xbp-1(zc12)+71. *p<0.0001.

Consistent with these data, the xbp-1(zc12) mutants provided herein are dramatically susceptible to the toxic effects of the immunostimulatory xenobiotic R24 in a developmental assay compared to control nematodes. FIG. 16. Thus, there are likely several mechanisms in nematodes to ensure immune homeostasis and promote tolerance during infection. For example, the UPR functions to protect the nematode from the ER stress, which occurs as a consequence of p38 MAPK activation and gain-of-function alleles in nsy-1 suggests that p38 MAPK PMK-1-mediated transcriptional responses are controlled via upstream mechanisms that negatively regulate immune activation at the level of NSY-1.

The human homolog of NSY-1, ASK1, regulates p38 activity through at least three conserved protein domains: a central serine-threonine kinase domain and two coiled-coil domains in the N and C termini, respectively. FIG. 10A; and Bunkoczi et al., "Structural and functional characterization of the human protein kinase ASK1" *Structure* 15:1215-1226. (2007). The N-terminal domain binds thioredoxin (TRX), which inhibits the function of NSY-1. Interestingly, the gain-of-function ums8 mutation, in which the negatively charged Arg is substituted for Gln, an uncharged amino acid with a large polar side chain, is located in a strongly conserved region, eight amino acids upstream of the region in NSY-1 predicted by homology to encode this N-terminal regulatory domain. FIG. 10A.

In some embodiments, the present invention contemplates that the activity of *C. elegans* NSY-1 is normally controlled by negative regulatory factors which, for example, may bind to the N-terminal coiled-coil domain. Thus, disruption of this region by a ums8 mutation could account for the constitutive activation of p38 MAPK immune effectors resulting in a pathogen resistance phenotype and toxicity to developing nematodes. There are five thioredoxin (TRX) homologs in *C. elegans* and that are also contemplated to function as negative regulators of NSY-1.

IV. Pharmaceutical Compositions/Formulations

The present invention further provides pharmaceutical compositions and/or formulations (e.g., comprising the compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the compound is administered in maintenance doses, ranging from 0.01 µg to 100 g per kg of body weight, once or more daily, to once every 20 years.

V. Small Organic Molecule Inhibitors

In some embodiments, the present invention provides drugs (e.g., small organic molecule inhibitors) that result in a hyperimmune state in nematodes (i.e., for example, via inhibition of the p38 MAP kinase pathway). In some embodiments, small molecule drugs are identified using the drug screening methods described herein. In preferred embodiments, the small molecule drugs of the present invention result in the death of nematodes, but not normal mammalian cells. In some embodiments, small molecule drugs are identified using the drug screens described herein.

In some embodiments, the present invention provides drug screening assays (e.g., to screen for antihelminthic drugs). The present invention is not limited to a particular mechanism. Indeed, an understanding of the mechanism is not necessary to practice the present invention. The present invention provides drug screening methods for identifying compounds that bind to a receptor protein expressed on a cell surface membrane (e.g., a nematode membrane).

In one embodiment, the invention contemplates a method for screening an effective nonpeptide small-molecule inhibitor that blocks/inhibits/prevents/disrupts a p38 MAP kinase pathway receptor (i.e., for example, ORLN-1). These molecules may be discovered using any one of several high-throughput screening methods. Stockwell, B. R., "Exploring biology with small organic molecules" Nature 432:846-854 (2004); Kay et al., "High-throughput screening strategies to identify inhibitors of protein-protein interactions" Mol. Diversity 1:139-140 (1996); Pfleger et al., "Extended bioluminescence resonance energy transfer (eBRET) for monitoring prolonged protein-protein interactions in live cells" Cell Signaling 18:1664-1670 (2006); Jung et al., "Surface plasmon resonance imaging-based protein arrays for high-throughput screening of protein-protein interaction inhibitors" Proteomics 5: 4427-4431 (2005); Nieuwenhuijsen et al., "A dual luciferase multiplexed high-throughput screening platform for protein-protein interactions" J. Biomol. Screen 8:676-684 (2003); and Berg, T., "Modulation of protein-protein interactions with small organic molecules" Angew. Chem. Int. Ed. Engl. 42:2462-2481 (2003).

EXPERIMENTAL

Example I

ORLN-1 Receptor Inhibitor Screening

To identify an inhibitor of OLRN-1, a GPCR screening programs can be employed. Osmond et al., *J Biomol Screen* 10:730-737 (2005); and Zhang et al., *Acta Pharmacol Sin* 33:372-384 (2012). OLRN-1 may be expressed in a heterologous expression system (e.g., Chinese hamster ovary (CHO) cells) and can transfect a cell line with a promiscuous or chimeric G-protein. This transfection may redirect the signaling pathway and lead to changes in intracellular $Ca^{2+}$ concentration that can readily be detected with cell-permeable $Ca^{2+}$-sensitive fluorescent dyes.

This approach does not require prior knowledge of the G-proteins or signaling pathways that are normally engaged by OLRN-1.

After validation, a library of compounds can be screened that has been specifically designed to identify modulators of GPCR activity, in particular, for those that inhibit the activity of OLRN-1. As a secondary screen, the identified compounds can be determined as to whether they are immunostimulatory and toxic to nematodes.

Selectivity for the nematode GPCR OLRN-1 can be determined using a counter screen by developing a heterologous screening system, similar to that described above, for a GPCR that is normally expressed in the human intestine (the site of action of antihelminthic medications), such as the somatostatin receptor. Compounds that inhibit OLRN-1 function and are toxic to *C. elegans*, but do not inhibit the intestinal GPCR can then be prioritized.

Example II

Small Molecule Inhibitor Development Using Structure Activity Relationships of R24

Forty-five (45) commercially available structural analogs of R24 have been identified for iterative SAR analysis. In studying these analogs, more potent and toxic immune stimulators than R24 can be identified.

A *C. elegans*-based assay are utilized for these approaches including but not limited to, i) testing brood size; ii) developmental rate; and iii) lifespan. Based on these results, additional analogs may be designed that will identify operative SARs that identify even more potent R24 analogs.

Nematocidal activity of different combinations of these molecules and known anti-helminthics (e.g. ivermectin and albendazole) can be tested to identify those that have synergistic activity. For example, antihelminthic efficacy of chemical inducers of the UPR (e.g. tunicamycin) can be used. Preliminary data suggests that these compounds may act synergistically with immunostimulatory molecules to kill nematodes (supra).

Example III

Efficacy Testing of Small Molecule Inhibitors Against Pathogenic Nematodes

To evaluate the in vitro and in vivo efficacy of the nematocidal compounds (and/or drug combinations) pathogenic nematode infection in vitro or in vivo animal models (e.g., for example, hamsters) are used. Hu, et al. PNAS USA 107:5955-5960 (2010); and Cappello, et al. PNAS USA 103:15154-15159 (2006).

Lead antihelminthic compounds are evaluated, either alone or in combination, to determine if they have in vitro nematocidal efficacy against model pathogenic nematodes by assessing parameters including, but not limited to, lifespan, motility, developmental rate and brood size.

New compounds can be tested for in vivo efficacy against pathogenic nematodes by evaluation against *Heligmosomoides bakeri* (formerly polygyrus) infection, which is a natural intestinal roundworm parasite of mice. Hu et al. *PLoS Negl Trop Dis* 4:e614 (2010).

Example IV

*C. elegans* and Bacterial Strains

*C. elegans* were grown and propagated on NGM plates with *E. coli* OP50, as previously described. Brenner, S., "The genetics of *Caenorhabditis elegans*" *Genetics* 77:71-94 (1974). AU307, an N2 Bristol-derived strain carrying the agIs44 transgene (pF08G5.6::GFP::unc-54-3'UTR; pmyo-2::mCherry), which was outcrossed to the wild-type strain N2 five times, was used as a wild-type strain, unless otherwise noted. Pukkila-Worley et al. (2014); and FIG. 9.

Previously isolated and characterized mutants used herein were: nsy-1(ag3) II, tir-1(qd4) III, xbp-1(zc12) III; zcIs4 V, pmk-1(km25) IV and zcIs4 V. Kim et al., "A conserved p38 MAP kinase pathway in *Caenorhabditis elegans* innate immunity" *Science* 297:623-626 (2002); Shivers et al., "Tissue-Specific Activities of an Immune Signaling Module Regulate Physiological Responses to Pathogenic and Nutritional Bacteria in *C. elegans*" *Cell Host Microbe* 6:321-330 (2009); and Calfon et al., "IRE1 couples endoplasmic reticulum load to secretory capacity by processing the XBP-1 mRNA" *Nature* 415:92-96 (2002).

Mutations isolated herein are: RPW1 [xts-1 nsy-1(ums1) II], RPW2 [xts-2 tir-1(ums2) III], RPW3 [xts-3 tir-1(ums3) III], RPW4 [xts-4 pmk-1(ums4) IV], and RPW5 [xts-5 sek-1(ums5) X] and RPW43 [agIs44; nsy-1(ums8)].

Example V

Isolation and Identification of Nematode Mutants

Mutagenesis of wild-type N2 animals was performed with ethyl methane sulfonate (EMS, Sigma-Aldrich Co.) following standard methods. Jorgensen et al., "The art and design of genetic screens: *Caenorhabditis elegans*" *Nat Rev Genet* 3:356-369 (2002). In two separate rounds of EMS screening, F2 animals from approximately 100,000 mutagenized haploid genomes were synchronized by hypochlorite treatment and plated onto "slow kill" media containing 140 μM of R24. Tan et al., "Killing of *Caenorhabditis elegans* by *Pseudomonas aeruginosa* used to model mammalian bacterial pathogenesis" *Proc Natl Acad Sci USA* 96:715-720 (1999). Previous studies had used 70 μM R24 to characterize the compounds' immunostimulatory properties. Pukkila-Worley et al., "Stimulation of host immune defenses by a small molecule protects *C. elegans* from bacterial infection" *PLoS Genet.* 8: e1002733 (2012). This lower concentration also delayed the development of wild-type nematodes, but the phenotype was more pronounced at an R24 concentration of 140 μM.

Nematodes that reached at least the L4 larval stage after approximately 60 hours at 20° C. were singled to a new plate. One hundred percent of unmutagenized nematodes treated in parallel were at the L2 or L3 larval stage at this time point. Five nematode mutants with the most penetrant Xts phenotypes after three rounds of retesting were identified using next-generation sequencing technology (Illumina, Inc.) following an established method. Sarin et al., "*Caenorhabditis elegans* mutant allele identification by whole-genome sequencing" *Nat. Methods* 5: 865-867 (2008). Briefly, the progeny from individual F2 recombinant animals that had the mutant phenotype following a 1× backcross to N2 animals were pooled for ums3, ums4 and ums5 (40, 38 and 33 pooled recombinants, respectively).

DNA was isolated from these samples using the Gentra Puregene Kit (Qiagen) and from the original ums1 and ums2 mutants. Libraries for deep sequencing were prepared using the NEBNext DNA Library Prep Reagent Set and Oligos (New England Biolabs, Inc.) and sequenced using Illumina HiSeq 2500 following instructions from the manufacturer.

Homozygous variants from the WS220 (ce10) *C. elegans* reference genome were identified using CloudMap (Minevich et al. 2012) and removed from further analysis if they were present in the unmutagenized parent wild-type N2 strain, the genome of which was also sequenced.

Example VI

Isolation and Identification of an F08G5.6::GFP Constitutive Activator

EMS mutagenesis was performed on strain agIs44 as described above. Synchronized F1 progeny from approximately 170,000 mutagenized haploid genomes were screened for animals that constitutively express agIs44 GFP fluorescence using a dissecting microscope that is able to visualize GFP. A single mutant allele, ums8, was identified.

To identify this ums8 mutation, DNA was isolated and sequenced using the methods described above. Pools of progeny from a total of 52 individual recombinants from a single outcross to wild-type N2 and from 43 individual recombinants that were outcrossed twice to N2 were sequenced. All recombinants selected for sequencing constitutively expressed agIs44 GFP fluorescence. Homozygous variants from WS220 (ce10) C. elegans reference genome that were present in both the 1× and 2× backcross samples, but were not present in the parent agIs44 strain, were identified using CloudMap (Minevich et al. 2012).

Example VII

Production of nsy-1 RNAi

Two RNAi constructs were created using 731 bp and 1,007 bp segments of nsy-1 coding region (bases 32,533 to 33,264 and 30,950 to 31,957 with respect to cosmid F59A6), which were amplified by PCR and subcloned into the Fire vector pPD129.36, ligation number L4440 (also referred to herein as L4440) to create plasmids pHC1 and pHC2, respectively.

These plasmids were transformed into the RNAi bacterial feeder strain HT115 and RNAi experiments were carried out with these strains following established protocols using HT115 bacteria expressing the empty vector L4440 as the control. Timmons et al., "Ingestion of bacterially expressed dsRNAs can produce specific and potent genetic interference in *Caenorhabditis elegans*" Gene 263:103-112 (2001).

For all RNAi experiments, L4 larval stage animals of the indicated genotypes were picked to RNAi bacteria and F1 progeny were used as indicated herein.

Example VIII nanoString nCounter Gene Expression and Quantitative RT-PCR

For nanoString transcription profiling, hypochlorite-synchronized L1 larval stage nematodes were added to NGM plates seeded with OP50. nsy-1(ums8) mutant nematodes were added to these plates approximately 24 hours before the nsy-1(ag3) and agIs44 nematodes, to allow the nematodes to reach the L4 larval stage at the time of harvest. The agIs44 nematodes were used as the wild-type control for this experiment. Nematodes were flash frozen in an ethanol and dry ice bath, lysed in 0.5% SDS, 5% β-mercaptoethanol, 10 mM EDTA, 10 mM Tris-HCl pH 7.4., 0.5 mg/mL Proteinase K at 55° C. for 15 minutes using a previously described protocol. Ding et al., "s-Adenosylmethionine Levels Govern Innate Immunity through Distinct Methylation-Dependent Pathways." *Cell Metab.* 22:633-645 (2015).

RNA was isolated using Tri-reagent (Sigma-Aldrich Co.) and 100 ng was analyzed by the nanoString nCounter Gene Expression System (nanoString Technologies, Inc.) using a "codeset" designed by nanoString that contained probes for one hundred eighteen (118) *C. elegans* genes. Table 2.

Probe hybridization, data acquisition and analysis were performed according to instructions from nanoString with the expression data from each sample normalized to the geometric mean of expression values for the control genes snb-1, ama-1 and act-1.

To determine the gene induction in nsy-1(ums8)/+heterozygotes, RNA was isolated from 100 L4 larval stage agIs44 (+1+), nsy-1(ums8)/nsy-1(ums8) homozygotes, and nsy-1(ums8)/+heterozygotes, the later of which were the F1 progeny from a cross between agIs44 animals and nsy-1 (ums8) homozygotes. RNA was isolated from three replicates using Trizol (Sigma-Aldrich Co.), treated with recombinant DNaseI (Ambion), and reverse transcribed to cDNA using the Retro-script kit (Life Technologies) and analyzed using iQ SYBR Green detection (Bio-Rad Laboratories, Inc.) in duplicate 20 μL reactions on a CFX1000 machine (Bio-Rad Laboratories, Inc.) with previously published primers. Troemel et al., "p38 MAPK regulates expression of immune response genes and contributes to longevity in *C. elegans*" *PLoS Genet.* 2:e183(2006); and Pukkila-Worley et al., "Immune defense mechanisms in the *Caenorhabditis elegans* intestinal epithelium" *Curr. Opin. Immunol.* 24 3-9 (2012). All values were normalized against the control gene snb-1. Fold change was calculated as previously described. Pfaffl, M. W., "A new mathematical model for relative quantification in real-time RT-PCR" *Nucleic Acids Res.* 29: e45 (2001).

For the other qRT-PCR studies, four L4 larval stage animals of the indicated genotype were added to RNAi bacteria and RNA was harvested from the mixed-stage F1 progeny from these nematodes. To ensure that nematodes would be approximately stage-matched at the time of harvest, nsy-1(ums8) mutants were allowed to lay their brood and develop at 20° C., while agIs44 and nsy-1(ag3) nematodes were kept at 15° C. RNA was isolated from three replicates using Tri-reagent (Sigma-Aldrich Co.), reversed transcribed into cDNA and studied by qRT-PCR following the protocol described above.

Example IX

Immunoblot Analyses

*C. elegans* were prepared in accordance with Example VIII to ensure that stage-matched animals at the young L4 larval stage were studied in each condition adapted for immunoblot analysis based upon a previously described protocol. Ding et al., "s-Adenosylmethionine Levels Govern Innate Immunity through Distinct Methylation-Dependent Pathways." *Cell Metab.* 22:633-645 (2015).

Harvested nematodes were washed twice with M9 buffer, incubated in a roller at room temperature for 15 minutes to allow the nematode intestine to clear of bacteria, washed an additional time and flash frozen in RIPA Buffer (Cell Signaling Technology, Inc.) using an ethanol and dry ice bath. Samples were lysed by sonication and centrifuged. Protein was quantified from the supernatant of each sample using Bradford Reagent (Bio-Rad Laboratories, Inc.). Laemmli buffer (Bio-Rad Laboratories, Inc.) was added to a concentration of 1× and the total protein from each sample was resolved on NuPage 4-12% gels (Life Technologies), transferred to nitrocellulose membranes (Life Technologies), blocked with 5% powdered milk in TBST and probed with a 1:2000 dilution of an antibody that recognizes the doubly phosphorylated TGY motif of PMK-1 (Promega Corporation).

The blot was then stripped and re-probed with a 1:10,000 dilution of an anti-actin antibody (Thermo Fisher Scientific, Inc.). Horseradish peroxidase (HRP)-conjugated anti-rabbit and anti-mouse IgG secondary antibodies (Thermo Fisher Scientific, Inc.) were used to detect the primary antibodies following the addition of ECL reagents (Thermo Fisher Scientific, Inc.), which were visualized using a Fujifilm LAS-400 luminescent image analyzer.

Example X

C. elegans Bacterial Infection and Development Assays

"Slow killing" *P. aeruginosa* infection assays were performed as previously described. Tan et al., "Killing of *Caenorhabditis elegans* by *Pseudomonas aeruginosa* used to model mammalian bacterial pathogenesis" *Proc Natl Acad Sci USA* 96:715-720 (1999).

A single colony of *P. aeruginosa* PA14 was inoculated into three mL of Luria-Bertani (LB) media and allowed to incubate at 37° C. for 14 to 15 hours. Ten μL of this culture was added to 35-mm tissue culture plates containing four mL of slow kill agar (0.35% peptone, 0.3% sodium chloride, 1.7% agar, 5 μg/mL cholesterol, 25 mM potassium phosphate, 1 mM magnesium sulfate, 1 mM calcium chloride). Plates were incubated for 24 hours at 37° C. and 24 hours at 25° C. 0.1 mg/mL 5-fluorodeoxyuridine (FUDR) was added to the media one to two hours before the start of the assay to prevent progeny from hatching.

Forty to fifty (40-50) nematodes at the young L4 larval stage were picked to each of three or four assay plates per experimental condition. *C. elegans* nematodes were prepared for the pathogenesis assays in accordance with Example VIII to ensure that the nematodes were stage-matched. Nematodes were scored as live or dead on a daily basis by gently touching them with a platinum wire. Nematodes that crawled onto the wall of the tissue culture plate were eliminated from the analysis. *P. aeruginosa* killing assays were conducted at 25° C.

Development assays were conducted by placing approximately 100 hypochlorite-synchronized L1 larval stage animals of the indicated genotype on "slow kill" media plates containing 140 μM R24 or the solvent control DMSO (1%) and monitoring development to the young adult stage for three days at 20° C. on two replicate plates per condition. FIG. 9. When development assays were conducted with RNAi bacteria, two L4 larval stage animals of the indicated genotype were allowed to lay their brood on RNAi bacteria at 15° C. FIG. 14B.

Plates were then transferred to 20° C. for three days. The stage of approximately three hundred (300) nematodes on each of three replicate plates per condition was recorded and the percentage of nematodes at the L4 larval stage was reported.

Representative nematodes from each condition were photographed. For the xbp-1(zc12) mutants, four nematodes were allowed to lay their brood for eight hours at 20° C. in the presence or absence of 70 μM R24. FIG. 16. *C. elegans* carrying the zcIs4 transgene were used as the control for these experiments.

Example XI

Microscopy

Nematodes were mounted onto 2% agar pads, paralyzed with levamisole (Sigma-Aldrich Co.) and photographed using a AXIO Imager Z1 microscope with a AxioCam HRm camera and Axiovision 4.6 software (Zeiss) or an Eclipse E400 with a DS-QiIMc camera and NIS Elements Imaging Software (Nikon Corporation). Photographs were acquired using the same imaging conditions for a given experiment and were processed in Photoshop (Adobe Systems, Inc.).

Example XII

Statistical Analyses and Amino Acid Alignment

Differences in survival of *C. elegans* animals in the *P. aeruginosa* pathogenesis assays were determined with the log-rank test. Fold changes in the qRT-PCR analyses and differences in the development of animals to the indicated stage were compared using unpaired, two-tailed student t-tests.

Amino acid alignment between human ASK1, the *Drosophila* Pk92B and *C. elegans* NSY-1 was determined using ClustalW2. Larkin et al., "Clustal W and Clustal X version 2.0" *Bioinformatics* 23:2947-2948 (2007).

Example XIII

Data Availability

Strains are available upon request. Accession numbers for genes and gene products are given for the publically available database Wormbase (www.wormbase.org). The accession numbers for the principal genes mentioned herein are: C17H12.8, C32H11.12, F08G5.6, F35E12.5, F56D6.2, nsy-1 (F59A6.1), pmk-1 (B0218.3), sek-1 (R03G5.2), tir-1 (F13B10.1), T24B8.5. Other accession numbers are given in Table 2.

I claim:

1. A method, comprising:
    a) providing:
        i) a patient exhibiting at least one nematode infection symptom;
        ii) a nematode comprising a p38 mitogen activated protein kinase immune response pathway, wherein said nematode lacks a toxic bacterial infection; and
        iii) a p38 mitogen activated protein kinase immune response pathway inducer selected from the group consisting of an RPW-24 compound, RPW-24 structural analogs and a cell surface G protein-coupled receptor RNAi molecule;
    b) administering said inducer to said patient; and
    c) reducing said at least one nematode infection symptom.

2. The method of claim 1, wherein said cell surface G protein-coupled receptor RNAi molecule targets a gene selected from the group consisting of orln, nsy, pmk, tir, sek and vhp.

3. The method of claim 1, wherein said p38 mitogen activated protein kinase immune response pathway activates an immune response.

4. The method of claim 1, wherein said p38 mitogen activated protein kinase immune response pathway inducer has specific affinity for a cell surface G protein-coupled receptor.

5. The method of claim 4, wherein said cell surface G protein-coupled receptor is an OLRN-1 receptor.

6. The method of claim 1, wherein said nematode is an adult nematode.

7. The method of claim 1, wherein said nematode is selected from the group consisting of *C. elegans, Ascaris lumbricoides, Necator americanus, Ancylostoma duodenale, Trichuris trichiura, Sirongyloides stercoralis, Onchocera, Wucheria bancrofti* and *Loa loa*.

8. A method, comprising:
    a) providing:
        i) a patient comprising a plurality of nematodes, wherein said plurality of nematodes comprise a p38 mitogen activated protein kinase immune response pathway and lacks a toxic bacterial infection; and ii) a p38 mitogen activated protein kinase immune response pathway inducer selected from the group consisting of an RPW-24 compound, RPW-24 structural analogs and a cell surface G protein-coupled receptor RNAi molecule;

b) administering said inducer to said patient;
c) hyperactivating said p38 mitogen activated protein kinase immune response pathway; and
d) killing at least a portion of said nematodes.

9. The method of claim 8, wherein said p38 mitogen activated protein kinase immune response pathway activates an immune response.

10. The method of claim 8, wherein said p38 mitogen activated protein kinase immune response pathway inducer has specific affinity for a cell surface G protein-coupled receptor.

11. The method of claim 10, wherein said cell surface G protein-coupled receptor is an OLRN-1 receptor.

12. The method of claim 8, wherein said cell surface G protein-coupled receptor RNAi molecule targets a gene selected from the group consisting of orln, nsy, pmk, tir, sek and vhp.

13. The method of claim 8, wherein said hyperactivating produces a nematode-toxic immune response.

14. The method of claim 8, wherein said method further comprises inducing a nematode endoplasmic reticulum unfolded protein response following administration of the p38 pathway inducer.

15. The method of claim 8, wherein said nematode is an adult nematode.

16. The method of claim 8, wherein said nematode is selected from the group consisting of *C. elegans, Ascaris lumbricoides, Necator americanus, Ancylostoma duodenale, Trichuris trichiura, Strongyloides stercoralis, Onchocera, Wucheria bancrofti* and *Loa loa*.

* * * * *